United States Patent
Ku et al.

(10) Patent No.: US 7,145,005 B2
(45) Date of Patent: Dec. 5, 2006

(54) 2-(6-{2-[(2R)-2-METHYL-1-PYRROLIDIN-1-YL]-ETHYL}-2-NAPHTHALEN-2-YL)-2H-PYRIDAZIN-3-ONE SALTS AND THEIR PREPARATION

(75) Inventors: Yi-Yin Ku, Buffalo Grove, IL (US); Timothy A. Grieme, Chicago, IL (US); Yu-Ming Pu, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 198 days.

(21) Appl. No.: 10/843,917

(22) Filed: May 12, 2004

(65) Prior Publication Data

US 2005/0256127 A1    Nov. 17, 2005

(51) Int. Cl.
*C07D 403/10* (2006.01)

(52) U.S. Cl. ......................... 544/238; 544/239; 548/579

(58) Field of Classification Search ................. 544/238, 544/239
See application file for complete search history.

(56) References Cited

U.S. PATENT DOCUMENTS

| | | | |
|---|---|---|---|
| 1,860,286 A | 5/1932 | Hartman et al. | |
| 3,489,756 A | 1/1970 | Bolhofer et al. | 260/247.7 |
| 3,639,476 A | 2/1972 | Eberle, et al. | 260/563 |
| 6,225,328 B1 | 5/2001 | Bernardon | 514/356 |
| 6,358,515 B1 | 3/2002 | Ogata et al. | 424/401 |

FOREIGN PATENT DOCUMENTS

| | | |
|---|---|---|
| CH | 149 007 | 11/1931 |
| DE | 556 324 | 8/1932 |
| GB | 1 122 756 | 8/1968 |
| GB | 1178400 | 1/1970 |
| WO | 94/17079 | 8/1994 |
| WO | 95/01426 | 1/1995 |
| WO | 95/09159 | 4/1995 |
| WO | 98/38156 | 9/1998 |
| WO | 98/57931 | 12/1998 |
| WO | 00/06254 | 2/2000 |
| WO | 00/27815 | 5/2000 |
| WO | 02/074758 | 9/2002 |
| WO | 03/093237 | 11/2003 |

OTHER PUBLICATIONS

Airaksinen et al., "Histamine Neurons in Human Hypothalamus: Anatomy in Normal and Alzeimer Diseased Brains," Neuroscience 44(2):465-481 (1991).

Andrés et al., "A Simple Steroselective Synthesis Of Enantiopure 2-Substituted Pyrrolidines and Piperidines From Chiral (R)-Phenylglycinol-Derived Bicyclic 1,3-Oxazolidines," Eur. J. Org. Chem. 1719-1726 (2000).

Aranyos et al., Novel Electron-Rich Bulky Phosphine Ligands Facilitate the Palladium-Catalyzed Preparation of Diaryl Ethers, J. Am Chem. Soc. 121:4369-4378 (1999).

Arrang, J-M., "Auto-inhibition of brain histamine release mediated by a novel class ($H_3$) of histamine receptor", Nature, 302:832-837 (1983).

(Continued)

*Primary Examiner*—Kahsay Habte
(74) *Attorney, Agent, or Firm*—Portia Chen

(57) ABSTRACT

The present invention relates to salts of 2-(6-{2-[(2R)-2-methyl-1-pyrrolidin-1-yl]-ethyl}-2-naphthalen-2-yl)-2H-pyridazin-3-one, processes for their preparation, pharmaceutical compositions comprising such compounds, method of using them, and a process for preparing the active agent.

4 Claims, 22 Drawing Sheets

OTHER PUBLICATIONS

Arrang, J-M., "Highly potent and selective ligands for histamine $H_3$-receptors", *Nature*, 327:117-128 (1987).

Bachman et al., "Quinoline Derivatives from 2- and 4-Chloroquinolines," Journal of Organic Chemistry, American Chemical Society. Easton, US 9:302-309 (1944).

Baston et al., "A New Route To 6-Aryl-Substituted 3, 4-Dihydronaphthalene Derivates Via Pd (O)-Catalyzed Cross-Coupling Reaction of Aryl Zinc Chlorides With an Aryl Triflate," Synthetic Communication 28(14):2725-2729 (1998).

Bjenning et al., "Peripherally Administered Ciproxifan Elevates Hypothalamic Histamine Levels And Potently Reduces Food Intake in the Sprague Dawley Rat," Histamine Research In The New Mellennium, Proceedings Of The International Sendai Histamine Symposium Held In Sendai, Japan, Nov. 22-25, 2000, p. 449-450.

Coutts et al., "Calmodulin. Antagonists as Potential Antifungal Agents," Pesticide Science, Elsevier Applied Science Publisher. Barking, GB 51(1):99-101 (1997).

Dai et al., "The First General Method For Palladium-Catalyzed Negishi Cross-Coupling Of Aryl And Vinyl Chlorides: Use of Commercially Available $Pd(P(t-Bu)_3)_2$ as a Catalyst," J. Am. Chem Soc. 123:2719-2724 (2001).

De Almeida et al., "Memory Facilitation by Histamine," Arch. Int. Pharmacodyn., 283:193-198 (1986).

Delaunois et al., "Modulation Of Acetylcholine, Capsaicin and Substance P Effects by Histamine $H_3$ Receptors in Isolated Perfused Rabbit Lungs," European Journal Of Pharmacology, 277:243-250 (1995).

Dimitriadou et al., "Functional Relationship Between Mast Cells and C-Sensitive Nerve Fibres Evidenced by Histamine $H_3$-Receptor Modulation in Rat Lung and Spleen," Clinical Science, 87:151-163 (1994).

Dohle et al., "Copper-Mediated Cross-Coupling of Functionalized Arylmagnesium Reagents with Functionalized Alkyl and Benzylic Halides," Organic Letters 3(18):2871-2873 (2001).

Duméry et al., "Development of Amygdaloid Cholinergic Mediation of Passive Avoidance Learning in the Rat," Exp. Brain. Res., 67:61-69 (1987).

Ellingboe et al., "Antihyperglycemic Activity of Novel Naphthalenyl 3*H*-1,2,3,5-Oxathiadiazole 2-Oxides," J. Med. Chem. 36:2485-2493 (1993).

Elworthy et al., "The Configurational Stability of Chiral Lithio α-Amino Carbanions. The Effect of Li-O vs. Li-N Complexation," Tetrahedron 50(20):6089-6096 (1994).

Fitzsimons et al., "Histamine Receptors Signalling in Epidermal Tumor Cell Lines With H-*ras* Gene Alterations," Inflamm. Res., 47, Supplement 1, S50-S51 (1998).

Fox et al., "Effects of Histamine $H_3$ Receptor Ligands GT-2331 And Ciproxifan in a Repeated Acquisition Response in the Spontaneously Hypertensive Rat Pup," Behavioural Brain Research 131:151-161 (2002).

Gaffield et al., "Chiroptical Properties of N-Nitrosopyrrolidines and N-Nitrosamino Acids," Tetrahedron 37:1861-1869 (1981).

Haas et al., Subcortical Modulation of Synaptic Plasticity in the Hippocampus, Behavioural Brain Research, 66:41-44 (1995).

Hartwig, "Transition Metal Catalyzed Synthesis of Arylamines and Aryl Ethers From Aryl Halides and Triflates: Scope And Mechanism," Angew. Chem. Int. Ed. 37:2046-2067 (1998).

Hatta et al., "Activation of Histamine $H_3$ Receptors Inhibits Carrier-Mediated Norepinephrine Release in a Human Model of Protracted Myocardial Ischemia[1,2]" The Journal Of Pharmacology And Experimental Therapeutics, 283(2):494-500 (1997).

Imamura et al., "Activation Of Histamine $H_3$-Receptors Inhibits Carrier-Mediated Norepinephrine Release During Protracted Myocardial Ischemia," Circulation Research, 78(3):475-481 (1996).

Imamura et al., "Histamine $H_3$-Receptor-Mediated Inhibition Of Calcitonin Gene-Related Peptide Release From Cardiac C Fibers," Circulation Research, 78(5):863-869 (1996).

Itoh et al., "Thioperamide, A Histamine $H_3$ Receptor Antagonist, Powerfully Suppresses Peptide YY-Induced Food Intake In Rats," Biol. Psychiatry 45:475-481 (1999).

Kamei et al., "Influence Of Certain $H_1$-Blockers On The Step-Through Active Avoidance Response In Rats," Psychopharmacology, 102:312-318 (1990).

Kamei et al., "Participation Of Histamine In The Step-Through Active Avoidance Response And Its Inhibition By $H_1$-Blockers," Japan J. Pharmacol., 57:473-482 (1991).

Karrer et al., Helvetica Chimica Acta. 34(270):2202-2210 (1951).

Kiyomori et al., "An Efficient Copper-Catalyzed Coupling Of Aryl Halides With Imidazoles," Tetrahedron Letters 40:2657-2660 (1999).

Klapars et al., "A General And Efficient Copper Catalyst For The Amidation of Aryl Halides And The *N*-Arylation Of Nitrogen Heterocycles," J. Am. Chem. Soc. 123:7727-7729 (2001).

Kwong et al., "Copper-Catalyzed Coupling Of Alkylamines And Aryl Iodides: An Efficient System Even In An Air Atmosphere," Organic Letters 4(4):581-584 (2002).

Leurs et al., "The Histamine $H_3$-Receptor: A Target For Developing New Drugs," Progress In Drug Research, 39:127-165 (1992).

Leurs et al., "The Medicinal Chemistry And Therapeutic Potentials Of Ligands Of The Histamine $H_3$ Receptor," Progress In Drug Research, 45:107-165 (1995).

Leurs et al., "Therapeutic Potential Of Histamine $H_3$ Receptor Agonists And Antagonists," Trends in Pharm. Sci, 19:177-183 (1998).

Levi et al., "Histamine $H_3$-Receptors: A New Frontier In Myocardial Ischemia," The Journal Of Pharmacology And Experimental Therapeutics, 292(3):825-830 (2000).

Li et al., "Highly Active, Air-Stable Versatile Palladium Catalysts For The C-C, C-N, And C-S Bond Formations Via Cross-Coupling Reactions Of Aryl Chlorides," J. Org. Chem. 66:8677-8681 (2001).

Li et al., "The First Phosphine Oxide Ligand Precursors For Transition Metal Catalyzed Cross-Coupling Reactions: C-C, C-N, And C-S Bond Formation On Unactivated Aryl Chlorides," Angew. Chem. Int. Ed. 40(8):1513-1516 (2001).

Lin et al., "Involvement Of Histaminergic Neurons In Arousal Mechanisms Demonstrated With $H_3$-Receptor Ligands In The Cat," Brain Research, 523:325-330 (1990).

Lipshutz et al., "Efficient Scavenging Of $Ph_3P$ And $Ph_3P=O$ With High-Loading Merrifield Resin," Organic Letters 3(12):1869-1871 (2001).

Lipshutz et al., "Substitution Reactions Of Aryl *Chlorides* With Organozinc Reagents Catalyzed By Ni(0)," Tetrahedron Letters 40:197-200 (1999).

Littke et al., "Versatile Catalysts For The Suzuki Cross-Coupling Of Arylboronic Acids With Aryl And Vinyl Halides And Triflates Under Mild Conditions," J. Am. Chem. Soc. 122:4020-4028 (2000).

Marcoux et al., "A General Copper-Catalyzed Synthesis Of Diaryl Ethers," J. Am. Chem. Soc. 119:10539-10540 (1997).

Matsubara et al., "UK-14,304, R(-) α-Methyl-Histamine And SMS 201-995 Block Plasma Protein Leakage Within Dura Mater By Prejunctional Mechanisms," European Journal Of Pharmacology, 224:145-150 (1992).

Mazurkiewicz-Kwilecki et al., "Changes In The Regional Brain Histamine And Histidine Levels In Postmortem Brains of Alzheimer Patients," Can. J. Physiol. Pharmacol, 67: 75-78 (1989).

McLeod et al., "Histamine $H_3$ Antagonists," Progress In Resp. Research 31:133-134 (2001).

Miyaura et al., "Palladium-Catalyzed Cross-Coupling Reactions Of Organoboron Compounds," Chem. Rev. 95:2457-2483 (1995).

Mohanakrishnan et al., "Pd(0)-Mediated Cross Coupling Of 2-Iodoestradiol With Organozinc Bromides: A General Route To The Synthesis Of 2-Alkynyl, 2-Alkenyl And 2-Alkylestradiol Analogs," Synlett. 7:1097-1099 (1999).

Molander et al., "Cross-Coupling Reactions Of Primary Alkylboronic Acids With Aryl Triflates And Aryl Halides," Tetrahedron 58:1465-1470 (2002).

Monti et al., "Effects Of Selective Activation Or Blockade Of The Histamine $H_3$ Receptor On Sleep And Wakefulness," European Journal Of Pharmacology, 205:283-287 (1991).

Monti et al., "Sleep And Waking During Acute Histamine $H_3$ Agonist BP2.94 Or $H_3$ Antagonist Carboperamide (MR 16155) Administration In Rats," Neuropsychopharmacology, 15(1):31-35 (1996).

Murakami et al., "AQ-0145, A Newly Developed Histamine $H_3$ Antagonist, Decreased Seizure Susceptibility Of Electrically Induced Convulsions In Mice," Meth. Find. Exp. Clin. Pharmacol. 17(C):70-73 (1995).

Nijhuis et al., "Stereochemical Aspects Of The "Tert-Amino Effect." 2. Enantio- And Diastereoselectivity In The Synthesis Of Quinolines, Pyrrolo[1,2-α]Quinolines, And [1,4]Oxazino[4,3-α]Quinolines," J. Org. Chem. 54:209-216 (1989).

Onodera et al., "Neuropharmacology Of The Histaminergic Neuron System In The Brain And Its Relationship With Behavioral Disorders," Progress In Neurobiology, 42:685-702 (1994).

Palomo et al., Phosphazene Bases For The Preparation Of Biaryl Thioethers From Aryl Iodides And Arenethiols, Tetrahedron Letters 41:1283-1286 (2000).

Palucki et al., "Palladium-Catalyzed Intermolecular Carbon-Oxygen Bond Formation: A New Synthesis Of Aryl Ethers," J. Am. Chem. Soc. 119:3395-3396 (1997).

Pan et al., "Histaminergic Ligands Attenuate Barrel Rotation in Rats Following Unilateral Labyrinthectomy," Meth. Find Exp. Clin. Pharmacol 20(9):771-777 (1998).

Panula et al., "Brain Histamine In Pathophysiological Conditions And Brain Diseases," The Histamine $H_3$ Receptor, 243-253 (1998).

Perez-Garcia et al., "Effects Of Histamine $H_3$ Receptor Ligands In Experimental Models Of Anxiety And Depression," Psychopharmacology 142:215-220 (1999).

Phillips et al., "Recent Advances In Histamine $H_3$ Receptor Agents," Annual Reports In Medicinal Chemistry, 33:31-40 (1998).

Rouleau, "Bioavailability, Antinociceptive And Antiiflammatory Properties Of BP 2-94, A Histamine $H_3$ Receptor Agonist Prodrug," The Journal Of Pharmacology And Experimental Therapeutics, 281(3):1085-1094 (1997).

Sakai et al., "Effects Of Thioperamide, A Histamine $H_3$ Receptor Antagonist, On Locomotor Activity And Brain Histamine Content In Mast Cell-Deficient W/W'Mice," Life Sciences, 48:2397-2404 (1991).

Schopfer et al., "A General Palladium-Catalysed Synthesis Of Aromatic And Heteroaromatic Thioethers," Tetrahedron 57:3069-3073 (2001).

Schwartz et al., "Histaminergic Transmission in the Mammalian Brain," Physiological Reviews 71(1):1-51 (1991).

Schwartz et al., "Histamine," Psychopharmacology: The Fourth Generation Of Progress, 397-405 (1995).

Shaywitz et al., "Dopaminergic But Not Noradrenergic Mediation Of Hyperactivity And Performance Deficits In The Developing Rat Pup," Psychopharmacology, 82:73-77 (1984).

Sugahara et al., "A Facile Copper-Catalyzed Ullmann Condensation: N-Arylation Of Heterocyclic Compounds Containing an -NHCO- Moiety," Chem. Pharm. Bull. 45(4):719-721 (1997).

Suzuki, "Recent Advances In The Cross-Coupling Reactions Of Organoboron Derivates With Organic Electrophiles, 1995-1998," Journal Of Organometallic Chemistry 576:147-168 (1999).

Szelag, "Role Of Histamine $H_3$-Receptors In The Proliferation Of Neoplastic Cells In Vitro," Med. Sci Monit., 4(5):747-755 (1998).

Tedford et al., "Cognition And Locomotor Activity In The Developing Rat: Comparisons Of Histamine $H_3$ Receptor Antagonists And ADHD Therapeutics," Society For Neuroscience Abstr., 22:22 (1996).

Tedford et al., "Pharmacological Characterization Of GT-2016, A Non-Thiourea-Containing Histamine $H_3$ Receptor Antagonist: In Vitro And In Vivo Studies," The Journal Of Pharmacology And Experimental Therapeutics, 275(2):598-604 (1995).

Tedford, "Clinical Application Of HA $H_3$ Receptor Antagonists In Learning And Memory Disorders," The Histamine $H_3$ Receptor 269-286 (1998).

Toshimitsu et al., "Preparation, Structure, And Reactivity Of Pentacoordinate Disilanes Bearing An 8-Charcogeno-1-Naphthyl Group And A Heteroatom On The Same Silicon Atom," Heteroatom Chemistry 12(5):392-397 (2001).

Vernsten et al., "Halogen Substituted Aryl Alkamine Ethers," Journal of the American Chemical Society 78:5398-5400 (1956).

Wada et al., Is The Histaminergic Neuron System A Regulatory Center For Whole-Brain Activity?, Trends In Neurosciences, 14(9):415-418 (1991).

Wear et al., "The Synthesis of Some Quinoxaline Derivatives," Jounral of the American Chemical Society 72:2893-2894 (1950).

Wolfe et al., "Rational Development Of Practical Catalysts For Aromatic Carbon-Nitrogen Bond Formation," Acc. Chem. Res. 37:805-818 (1998).

Wolfe et al., "Simple, Efficient Catalyst System For The Palladium-Catalyzed Amination Of Aryl Chlorides, Bromides, And Triflates," J. Org. Chem. 65:1158-1174 (2000).

Yamada et al., "A Biogenetic-Type Asymmetric Cyclization Syntheses Of Optically Active α-Cyclocitral And Trans-α-Damascone," Tetrahedron Letters 5:381-384 (1973).

Yamamoto et al., "Ullmann Condensation Using Copper Or Copper Oxide As The Reactant. Arylation Of Active Hydrogen Compound (Imides, Amides, Amines, Phenol, Benzoic Acid, And Phenylacetylene)," Can. J. Chem. 61:86-91 (1983).

Yang et al., "Palladium-Catalyzed Animation Of Aryl Halides And Sulfonates," Journal Of Organometallic Chemistry 576:125-146 (1999).

Yates et al., "Effects Of A Novel Histamine $H_3$ Receptor Antagonist, GT-2394, On Food Intake And Weight Gain In Sprague-Dawley Rats," Abstracts, Society For Neuroscience, 102.10:219 (Nov. 2000).

Yokoyama et al., "Effect Of Thioperamide, A Histamine $H_3$ Receptor Antagonist, On Electrically Induced Convulsions In Mice," Journal Of Pharmacology, 234:129-133 (1993).

Yokoyama et al., "Histamine And Seizures Implications For The Treatment Of Epilepsy," CNS Drugs, 5(5):321-330 (1996).

Zou et al., "Ag(I)-Promoted Suzuki-Miyaura Cross-Couplings Of N-Alkylboronic Acids," Tetrahedron Letters 42:7213-7215 (2001).

2-(6-{2-[(2R)-2-METHYL-1-PYRROLIDIN-1-YL]-ETHYL}-2-NAPHTHALEN-2-YL)-2H-PYRIDAZIN-3-ONE SALTS AND THEIR PREPARATION

BACKGROUND OF THE INVENTION

1. Technical Field

The invention relates to certain compounds having therapeutic utility and to processes for their preparation. More particularly, the present invention relates to salts of 2-(6-{2-[(2R)-2-methyl-1-pyrrolidin-1-yl]-ethyl}-2-naphthalen-2-yl)-2H-pyridazin-3-one, which demonstrates histamine-3 receptor ligand activity.

2. Description of Related Technology

Histamine-3 receptor ligands are recognized modulators of neuronal activity. One active agent, 2-(6-{2-[(2R)-2-methyl-1-pyrrolidin-1-yl]-ethyl}-2-naphthalen-2-yl)-2H-pyridazin-3-one, has been described as demonstrating histamine-3 modulating activity. 2-(6-{2-[(2R)-2-Methyl-1-pyrrolidin-1-yl]-ethyl}-2-naphthalen-2-yl)-2H-pyridazin-3-one has the structure

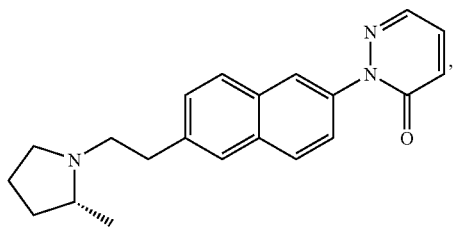

and is a useful therapeutic agent for treating a variety of histamine-3 mediated conditions and diseases. The compound also can have the name 2-(6-{2-[(2R)-2-methyl-1-pyrrolidinyl]ethyl}-2-naphthyl)-3(2H)-pyridazinone. The active agent is further described in at least U.S. patent application Ser. No. 10/689,735, filed on Oct. 22, 2003. The compound is stable at room temperature and can be isolated as a low melting point solid having a melting point of 58° C.

Salts of 2-(6-{2-[(2R)-2-methyl-1-pyrrolidin-1-yl]-ethyl}-2-naphthalen-2-yl)-2H-pyridazin-3-one that demonstrate crystalline properties are particularly beneficial for formulation of the active agent. Moreover, it would be particularly beneficial to identify forms of the 2-(6-{2-[(2R)-2-methyl-1-pyrrolidin-1-yl]-ethyl}-2-naphthalen-2-yl)-2H-pyridazin-3-one active agent that demonstrate crystalline properties and are characterized by improved stability and a melting point higher than the 2-(6-{2-[(2R)-2-methyl-1-pyrrolidin-1-yl]-ethyl}-2-naphthalen-2-yl)-2H-pyridazin-3-one active agent. Isolated forms of 2-(6-{2-[(2R)-2-methyl-1-pyrrolidin-1-yl]-ethyl}-2-naphthalen-2-yl)-2H-pyridazin-3-one demonstrating such properties would be particularly beneficial for preparing pharmaceutical formulations useful for preventing and treating histamine-3 mediated diseases and disorders.

SUMMARY OF THE INVENTION

Figure 1:
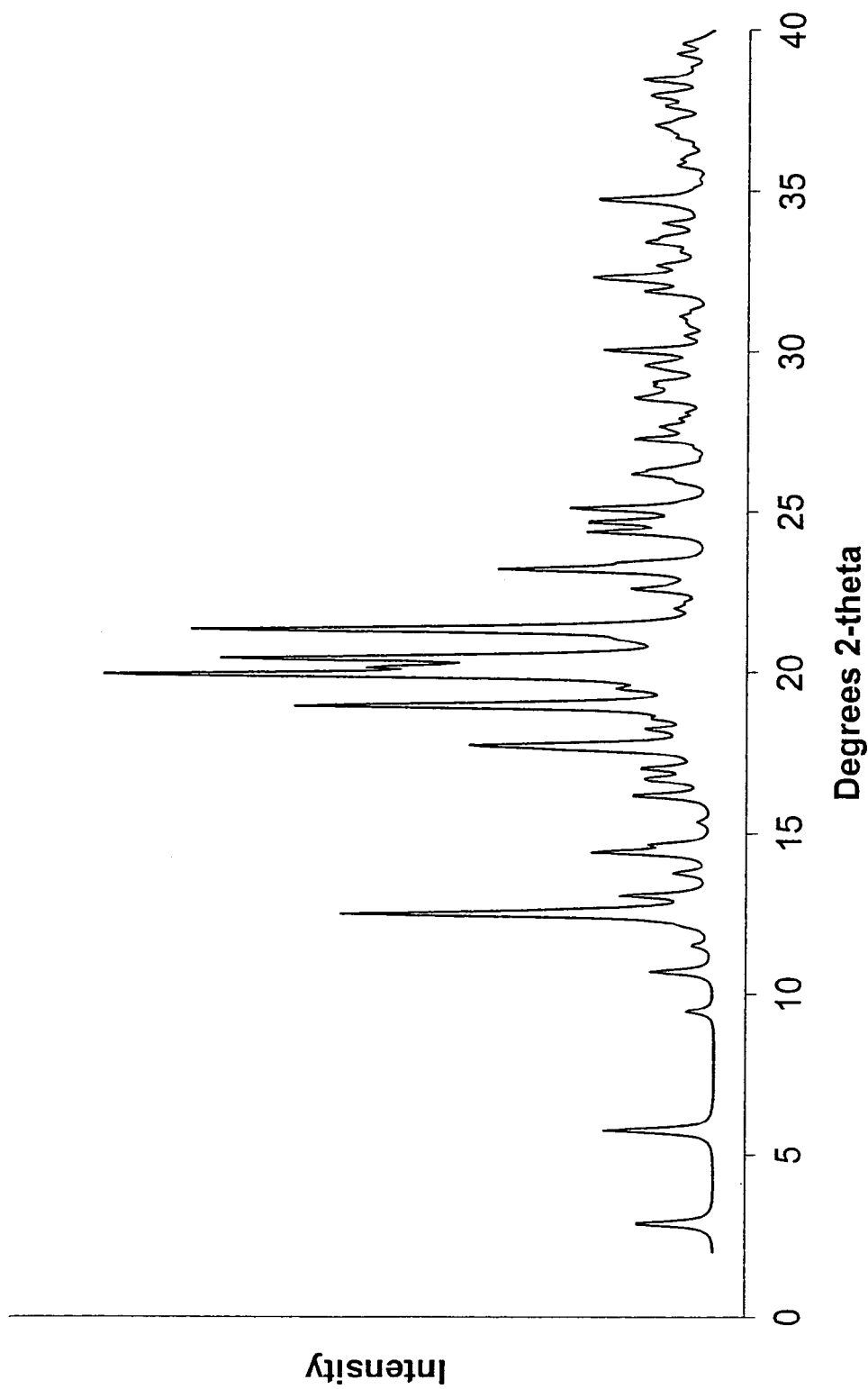
FIG. 1 is the powder X-ray diffractogram of 2-(6-{2-[(2R)-2-methyl-1-pyrrolidin-1-yl]-ethyl}-2-naphthalen-2-yl)-2H-pyridazin-3-one citrate (2:1 ratio).

The present invention is related to salts of 2-(6-{2-[(2R)-2-methyl-1-pyrrolidin-1-yl]-ethyl}-2-naphthalen-2-yl)-2H-pyridazin-3-one active agent. In one aspect, the present invention relates to salts of 2-(6-{2-[(2R)-2-methyl-1-pyrrolidin-1-yl]-ethyl}-2-naphthalen-2-yl)-2H-pyridazin-3-one, and more particularly isolated forms of these salts. The salts obtained can be substantially pure and demonstrate characteristic peaks as shown in their X-ray powder diffraction pattern. Processes for preparing such salts also are contemplated. In particular, the invention is directed to citrate salts, particularly those have a 2:1 citrate/molecule ratio and a 1:1 citrate/molecule ratio, hydrobromide salts, particularly crystal Form I and crystal Form II hydrobromide salts, maleate salts, fumarate salts, salicylate salts, sulfate salts, and tosylate salts of 2-(6-{2-[(2R)-2-methyl-1-pyrrolidin-1-yl]-ethyl}-2-naphthalen-2-yl)-2H-pyridazin-3-one.

The salts generally can be prepared according to the process comprising the steps of mixing a solution of 2-(6-{2-[(2R)-2-methyl-1-pyrrolidin-1-yl]-ethyl}-2-naphthalen-2-yl)-2H-pyridazin-3-one with an anionic acid; heating the solution to a desired temperature wherein the solids are dissolved in the solvent; cooling the resulting solution; and filtering the resulting solid at ambient temperature. As used herein, the term "ambient temperature" refers to temperatures from about 20° C. to about 25° C. at atmospheric pressure.

Another aspect of the invention, relates to the preparation of 2-(6-{2-methyl-1-pyrrolidin-1-yl]-ethyl}-2-naphthalen-2-yl)-2H-pyridazin-3-one active agent. The process comprises the steps of converting a trifluoro-methanesulfonic acid 6-bromo-naphthalen-2-yl ester to 2-bromo-6-vinyl-naphthalene; and reacting 2-bromo-6-vinyl-naphthalene with a 2-methylpyrrolidine anion generated with n-butyl-lithium to provide a 1-[2-(6-bromo-naphthalen-2-yl)-ethyl]-2-methyl-pyrrolidine compound, which is reacted with 2H-pyridazin-3-one in the presence of a copper catalyst and ligand to provide a 2-(6-{2-methyl-1-pyrrolidin-1-yl]-ethyl}-2-naphthalen-2-yl)-2H-pyridazin-3-one active agent.

In another aspect, the invention relates to a particularly beneficial process for preparing 2-(6-{2-methyl-1-pyrrolidin-1-yl]-ethyl}-2-naphthalen-2-yl)-2H-pyridazin-3-one citrate. The process generally comprises the steps of (a) dissolving 2-(6-{2-[(2R)-2-methyl-1-pyrrolidin-1-yl]-ethyl}-2-naphthalen-2-yl)-2H-pyridazin-3-one in a solution of citric acid and ethanol; (b) heating the reaction mixture to a temperature of about 40° C. to about 65° C.; (c) adding a seed slurry of 2-(6-{2-[(2R)-2-methyl-1-pyrrolidin-1-yl]-ethyl}-2-naphthalen-2-yl)-2H-pyridazin-3-one crystals; (d) cooling the resulting solution to less than 5° C. for at least one hour to provide a suspension; and (e) filtering the resulting suspension.

Yet another aspect of the invention relates to a method of treating a histamine-3 mediated disorder comprising the step of administering a therapeutically effective amount of 2-(6-{2-[(2R)-2-methyl-1-pyrrolidin-1-yl]-ethyl}-2-naphthalen-2-yl)-2H-pyridazin-3-one salt, a composition comprising the same, or a mixture containing the compound or composition, to a host mammal, particularly a human, in need of such treatment. More particularly, the method relates to administering citrate, hydrobromide, maleate, fumarate, salicylate, sulfate, and tosylate salts of 2-(6-{2-[(2R)-2-methyl-1-pyrrolidin-1-yl]-ethyl}-2-naphthalen-2-yl)-2H-pyridazin-3-one.

The compounds, compositions comprising the compounds, methods for making the compounds, and methods for treating and preventing conditions and disorders by administering the compounds are further described herein.

DETAILED DESCRIPTION OF THE INVENTION

Compounds of the Invention

Compounds of the invention are salts of the 2-(6-{2-[(2R)-2-methyl-1-pyrrolidin-1-yl]-ethyl}-2-naphthalen-2-yl)-2H-pyridazin-3-one active agent.

2-(6-{2-[(2R)-2-Methyl-1-pyrrolidin-1-yl]-ethyl}-2-naphthalen-2-yl)-2H-pyridazin-3-one citrate is solid that can be identified by its powder X-ray diffraction pattern in accordance with the Brief Description of the Drawings (FIG. 1). The 2-(6-{2-[(2R)-2-methyl-1-pyrrolidin-1-yl]-ethyl}-2-naphthalen-2-yl)-2H-pyridazin-3-one citrate more commonly is found as a citrate in a 2:1 citrate/molecule ratio.

Characteristic two-theta angles of the powder X-ray diffraction pattern for 2-(6-{2-methyl-1-pyrrolidin-1-yl]-ethyl}-2-naphthalen-2-yl)-2H-pyridazin-3-one citrate (2:1 ratio) are 2.7°±0.1°, 5.6°±0.1°, 9.3°±0.1°, 10.5°±0.1°, 11.3°±0.1°, 12.3°±0.1°, 12.9°±0.1°, 14.24°±0.1°, 17.5°±0.1°, 18.7°±0.1°, 19.7°±0.1°, 20.2°±0.1°, and 21.1°.

Figure 2:
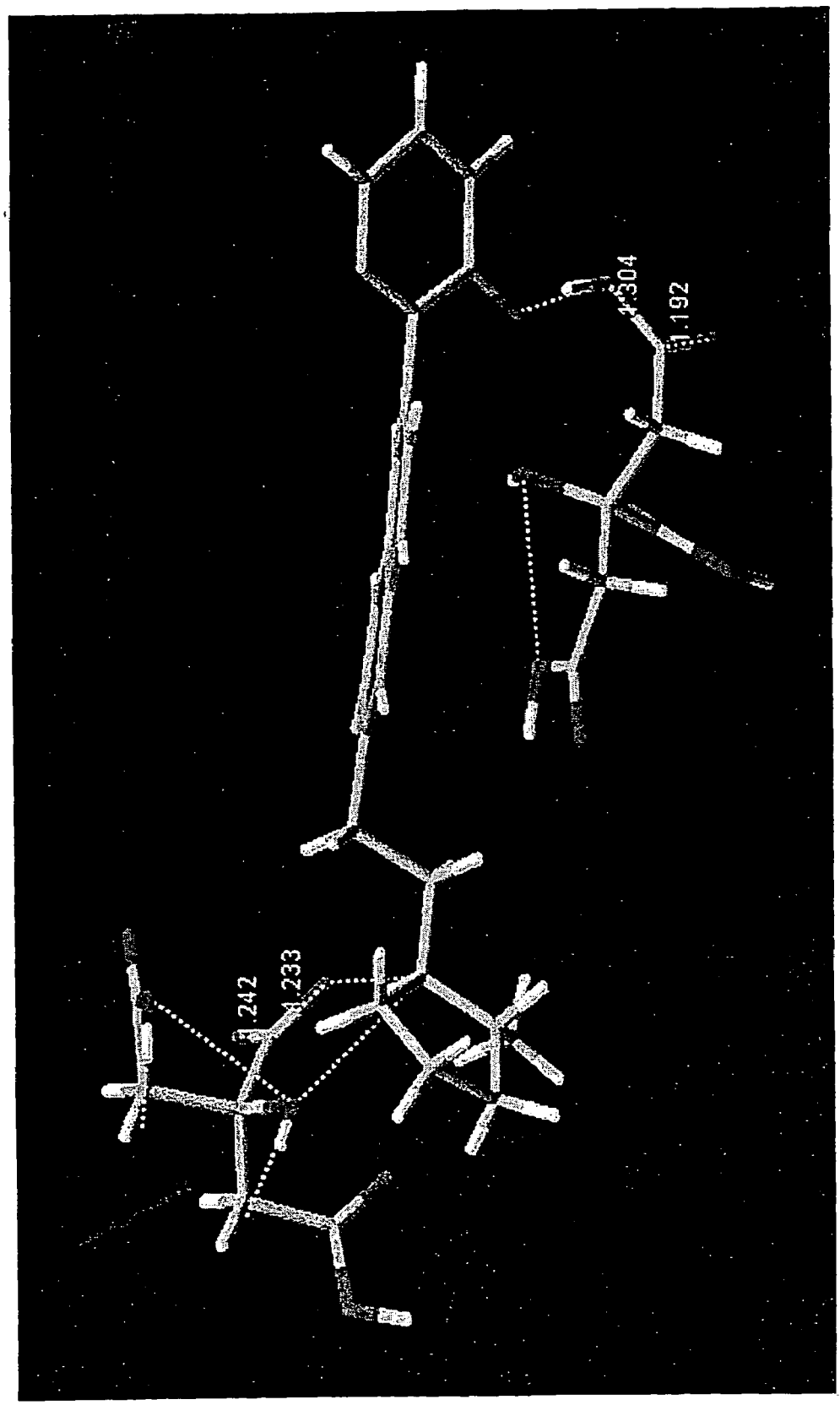
FIG. 2 depicts the crystal lattice arrangement of a 2-(6-{2-[(2R)-2-methyl-1-pyrrolidin-1-yl]-ethyl}-2-naphthalen-2-yl)-2H-pyridazin-3-one citrate (2:1 ratio) unit cell.

The crystal structure can be identified as a monocitrate citric acid co-crystal. As used herein, the term "co-crystal" refers to two different compounds crystallized together without chemical interaction. More specifically, in the monocitrate citric acid co-crystal, two molecules of a citric moiety inside the unit cell each independently accepts a proton from the base counterion or hydrogen bonds to a carboxylic acid moiety. The crystal lattice arrangement of the unit cell is depicted in FIG. 2.

The crystallographic unit cell parameters of a single salt citrate co-crystal have been determined as having the following parameters: a is 30.880 (10) Å; b is 9.809 (3) Å; c is 11.001 (3) Å; and β is 95.712 (5) Å. To afford a cell volume of 3315.5 (19) Å$^3$, wherein a, b, and c are each a representative length of the crystal lattice and β is the unique angle. The co-crystal crystallizes in the monoclinic space group P21.

The mono-citrate/citric acid complex of 2-(6-{2-[(2R)-2-methyl-1-pyrrolidin-1-yl]-ethyl}-2-naphthalen-2-yl)-2H-pyridazin-3-one forms a mono-citrate with a second citric acid molecule incorporated in an un-ionized state. Such state is evidenced by a lack of contact between the citric acid moiety and an ionizable moiety. The citrate molecule demonstrates close contact with the tertiary amine in the five-membered ring of the pyrrolidinyl moiety in the 2-(6-{2-[(2R)-2-methyl-1-pyrrolidin-1-yl]-ethyl}-2-naphthalen-2-yl)-2H-pyridazin-3-one. The citric acid molecule contacts only the oxygen atom of the amide group formed from the amine moiety of 2-(6-{2-[(2R)-2-methyl-1-pyrrolidin-1-yl]-ethyl}-2-naphthalen-2-yl)-2H-pyridazin-3-one. The amine serves as a basic partner for the citrate, however, the amide oxygen is not basic in character and does not readily provide a ionizable partner for the citric acid molecule. In addition, the oxygen-carbon bond lengths of the citric acid groups are very unequal (1.304 Å and 1.194 Å) indicating that the charged resonant structure is not present. In contrast, typically, when a charged state is present for an organic acid, a resonant bond state develops and the two oxygen-carbon bonds become nearly equal as they are in the citrate of this crystal form (1.242 Å and 1.233 Å). Such nature of the citrate co-crystal is depicted below:

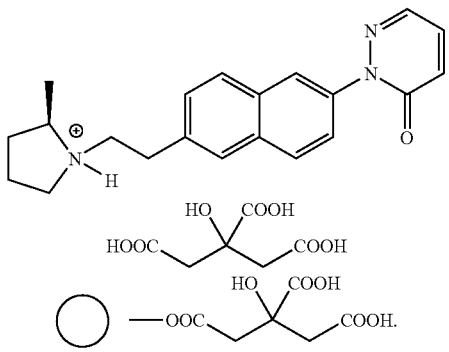

Figure 2A:
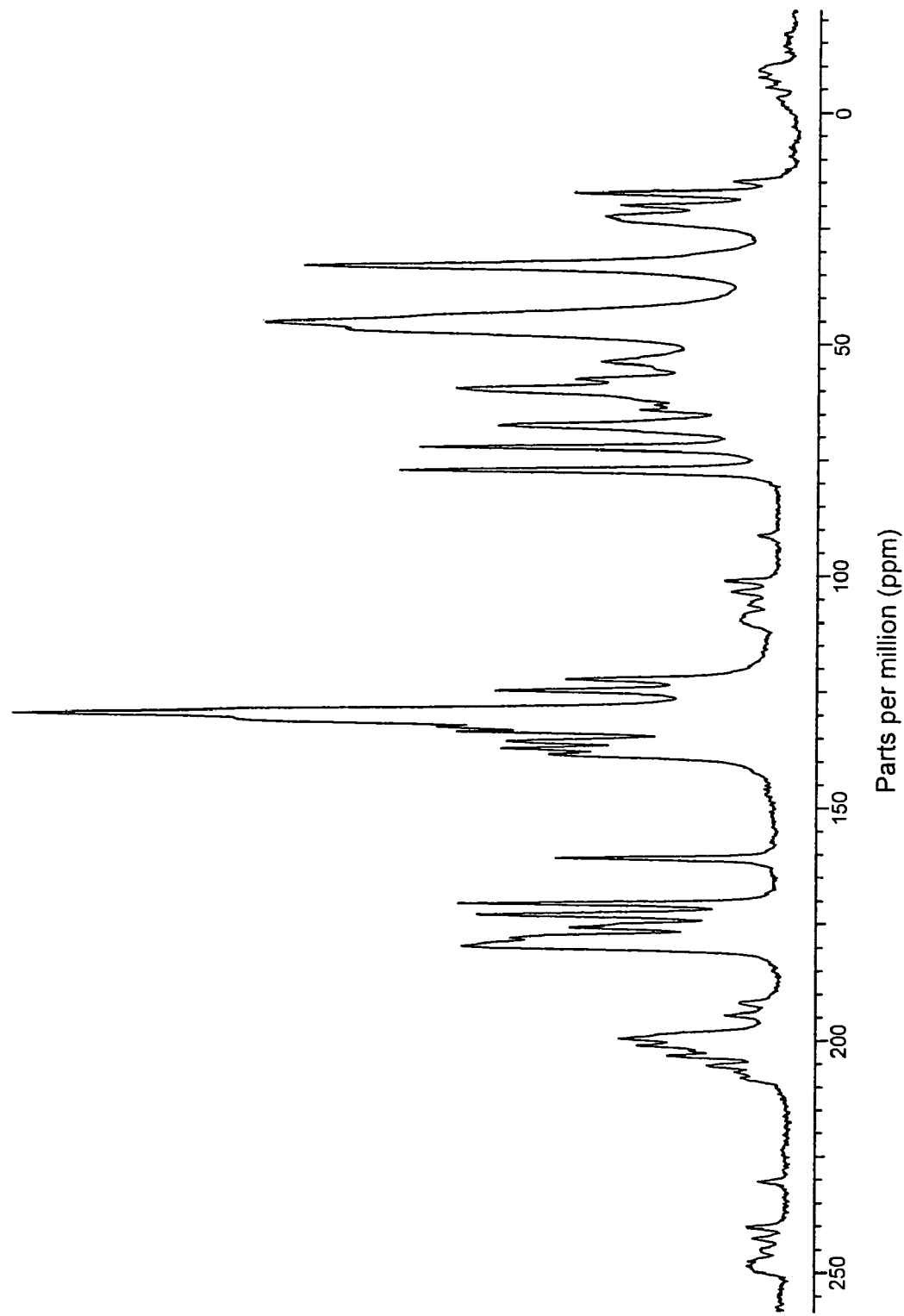
FIG. 2A is the solid state $^{13}$C NMR spectra of a 2-(6-{2-[(2R)-2-methyl-1-pyrrolidin-1-yl]-ethyl}-2-naphthalen-2-yl)-2H-pyridazin-3-one citrate (2:1 ratio) unit cell.

Solid state $^{13}$Carbon NMR analysis demonstrates that 2-(6-{2-[(2R)-2-methyl-1-pyrrolidin-1-yl]-ethyl}-2-naphthalen-2-yl)-2H-pyridazin-3-one citrate showed characteristic $^{13}$C NMR at δ 179.9, 179.1, 177.9, 175.9,. 175.2, 173.1, 170.7, 160.9, 138.7, 137.4, 135.9, 133.8, 132.8, 131.4, 130.2, 129.4, 125.0, 122.4, 77.5, 72.5, 67.8, 59.7, 57.6, 54.0, 47.1, 45.8, 44.2, 33.4, 23.6, 22.6, 20.2, 17.5, and 14.9. The $^{13}$Carbon NMR spectrum is shown in FIG. 2A.

To further confirm the structure of the 2-(6-{2-[(2R)-2-methyl-1-pyrrolidin-1-yl]-ethyl}-2-naphthalen-2-yl)-2H-pyridazin-3-one citrate in the crystal, NMR analysis demonstrates that the citrate salt showed characteristic $^1$H NMR in DMSO-$d_6$ at δ 8.2–8.1 (2H, m), 8.0–7.9 (2H, t), 7.9–7.8 (1H, s), 7.7–7.6 (1H, dd), 7.6–7.5 (2H, m), 7.2–7.1 (1H, dd), 3.7–3.5 (2H, m), 3.5–3.4 (1H, m), 3.4–3.1 (4H, m), 2.7–2.5 (8H, dd), 2.3–2.1 (1H,m), 2.1–1.9 (2H, m), 1.7–1.6 (1H, m), 1.4–1.3 (3H, d).

Standard $^{13}$Carbon NMR analysis demonstrates that 2-(6-{2-[(2R)-2-methyl-1-pyrrolidin-1-yl]-ethyl}-2-naphthalen-2-yl)-2H-pyridazin-3-one citrate showed characteristic $^{13}$C NMR in DMSO-$d_6$ at δ 175.1, 170.6, 158.9, 138.4, 137.2, 135.3, 132.0, 128.0, 127.5, 127.3, 126.4, 123.7, 123.4, 71.7, 63.1, 52.6, 43.6, 31.4, 31.0, 21.2, 15.8 with 3 peaks overlapping.

Mass spectroscopy analysis of 2-(6-{2-[(2R)-2-methyl-1-pyrrolidin-1-yl]-ethyl}-2-naphthalen-2-yl)-2H-pyridazin-3-one citrate demonstrates MS-DCI (M+H)$^+$ at m/z 334.2 (fragment at 210.0).

Figure 3:
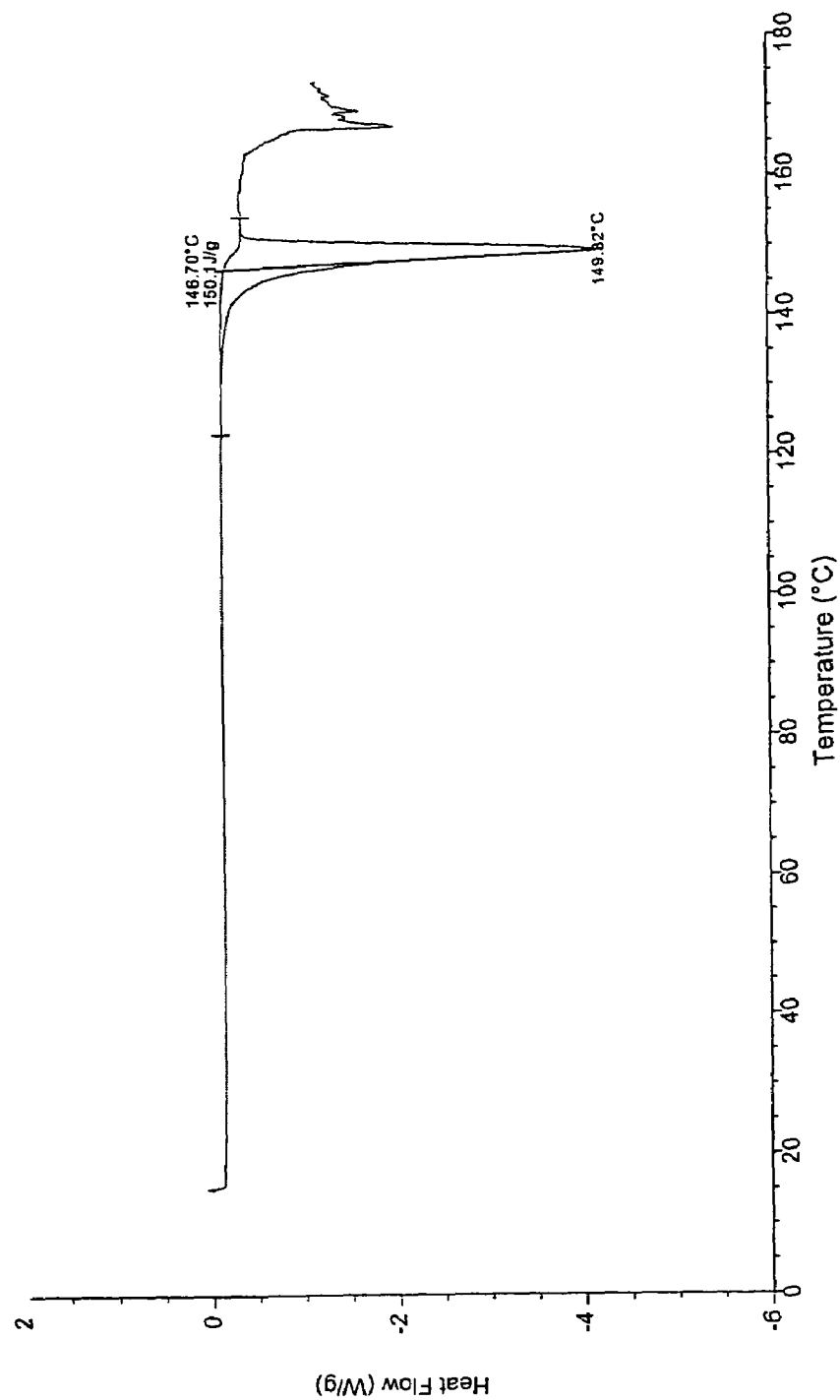
FIG. 3 is the differential scanning calorimetry (DSC) thermogram of 2-(6-{2-[(2R)-2-methyl-1-pyrrolidin-1-yl]-ethyl}-2-naphthalen-2-yl)-2H-pyridazin-3-one citrate (2:1 ratio).

Differential scanning calorimetery analysis confirms that the melting point of 2-(6-{2-[(2R)-2-methyl-1-pyrrolidin-1-yl]-ethyl}-2-naphthalen-2-yl)-2H-pyridazin-3-one citrate (2:1 ratio) is 143° C. to 147° C. (FIG. 3).

Figure 3A:
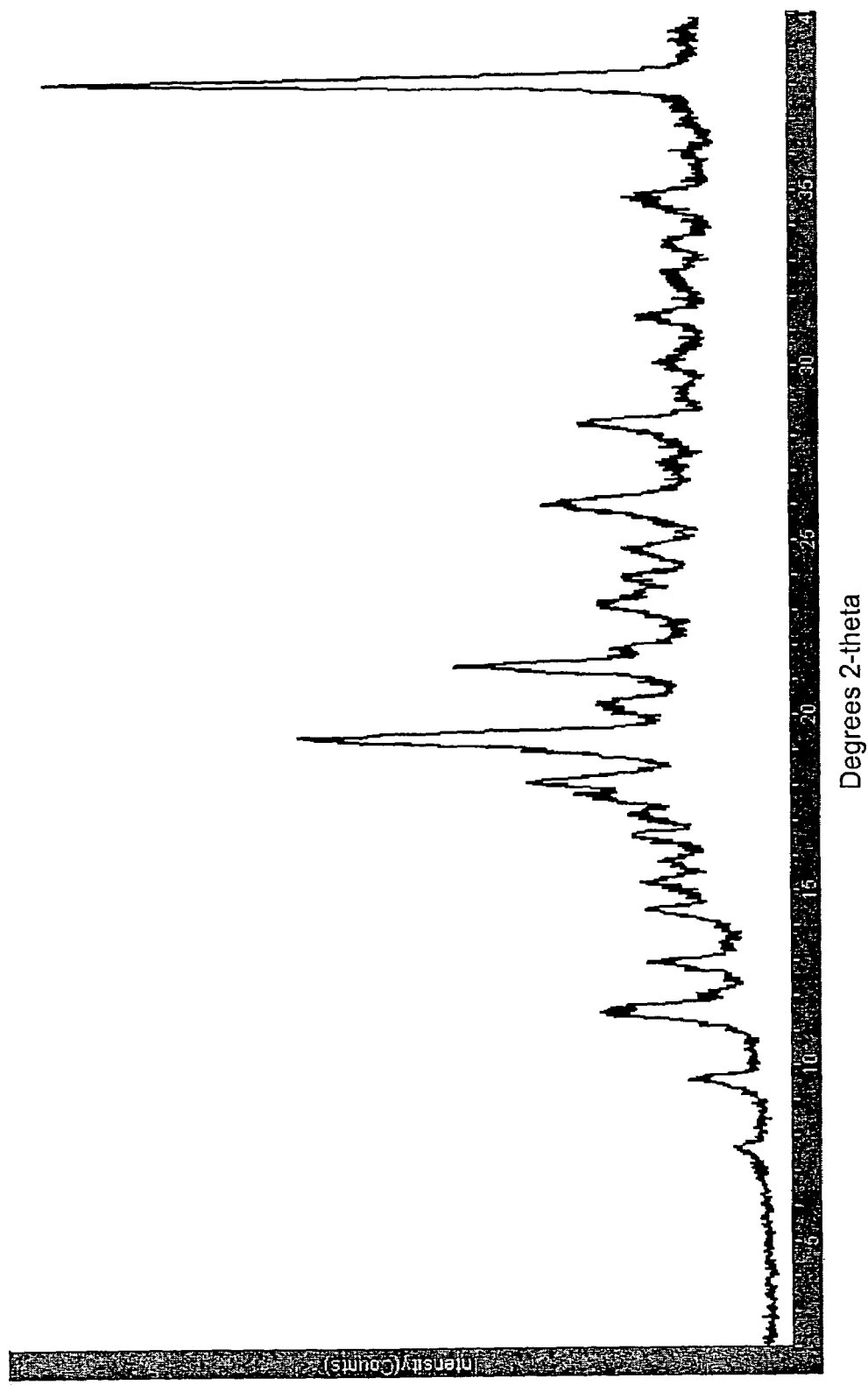
FIG. 3A is the powder X-ray diffractogram of 2-(6-{2-[(2R)-2-methyl-1-pyrrolidin-1-yl]-ethyl}-2-naphthalen-2-yl)-2H-pyridazin-3-one citrate (1:1 ratio).
Figure 4:
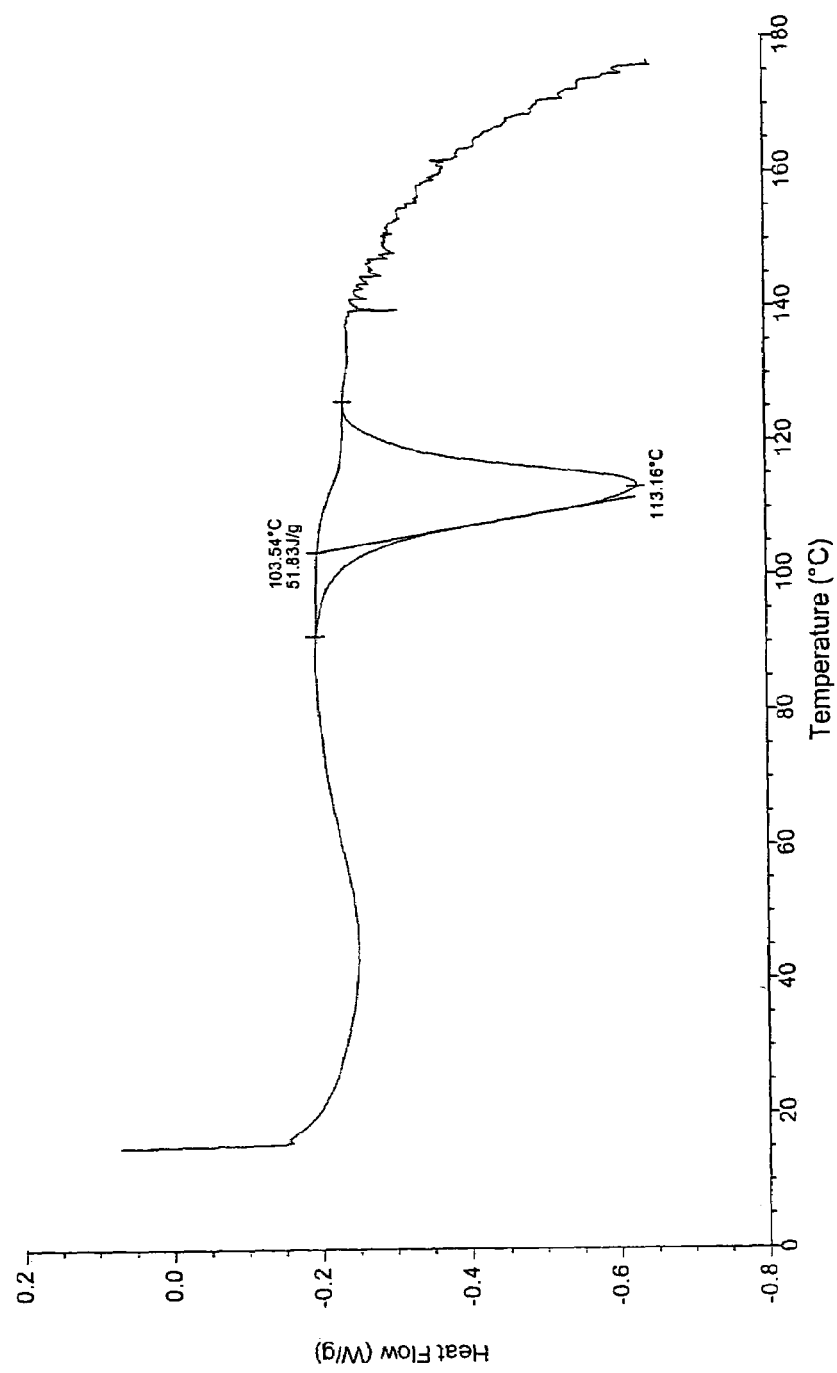
FIG. 4 is the differential scanning calorimetry thermogram of 2-(6-{2-[(2R)-2-methyl-1-pyrrolidin-1-yl]-ethyl}-2-naphthalen-2-yl)-2H-pyridazin-3-one citrate (1:1 ratio).

The powder X-ray diffraction pattern of 2-(6-{2-[(2R)-2-methyl-1-pyrrolidin-1-yl]-ethyl}-2-naphthalen-2-yl)-2H-pyridazin-3-one citrate (1:1 ratio) demonstrate characteristic 2-theta angles of: 7.658°±0.1°, 9.560°±0.1°, 11.520°±0.1°, 19.437°±0.1° and 21.440°±0.1° (FIG. 3A). The melting point of 2-(6-{2-[(2R)-2-methyl-1-pyrrolidin-1-yl]-ethyl}-2-naphthalen-2-yl)-2H-pyridazin-3-one citrate (1:1 ratio) as determined by DSC analysis is 103° C.–113° C. (FIG. 4).

Figure 5:
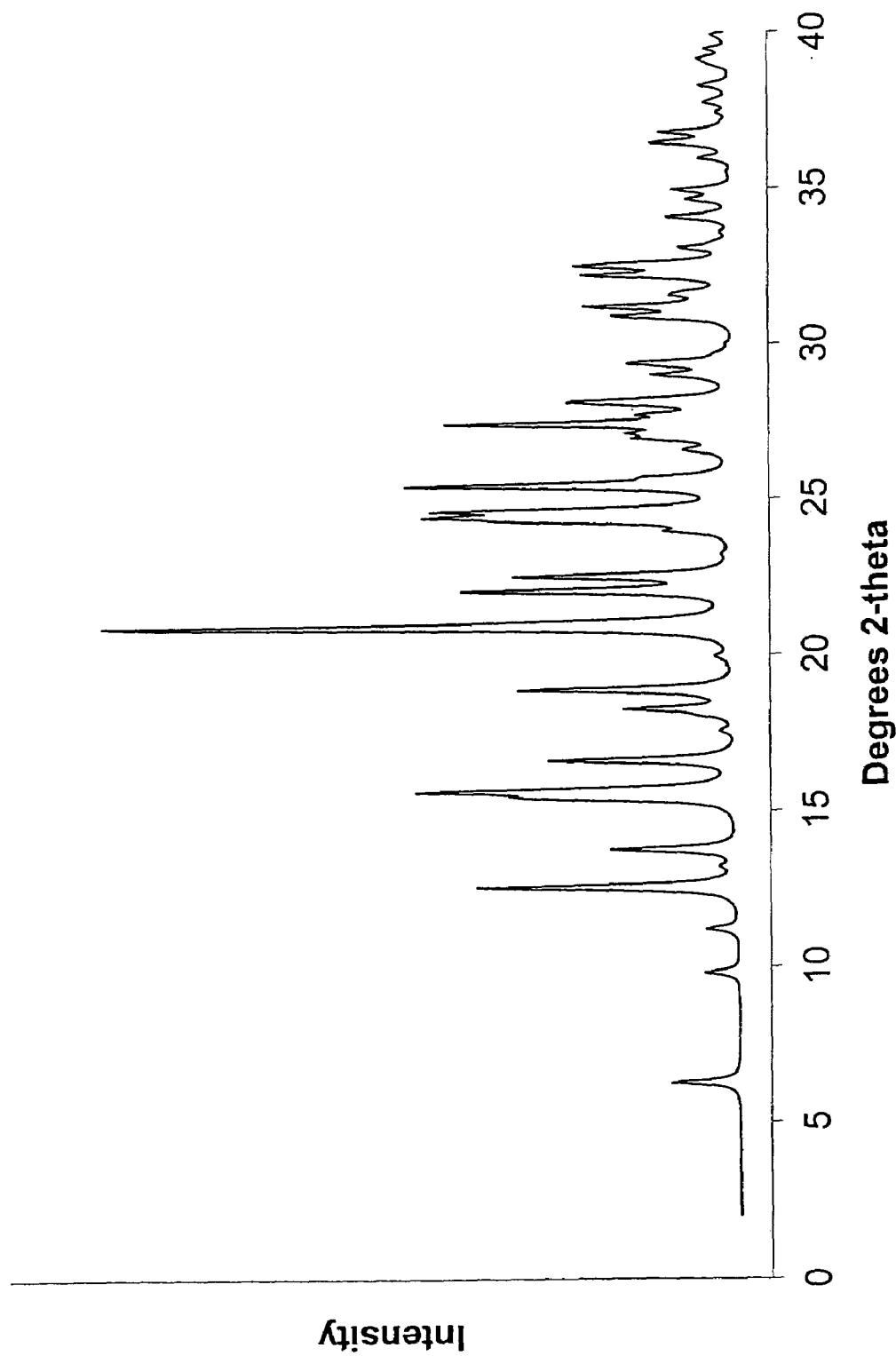
FIG. 5 is the powder X-ray diffractogram of 2-(6-{2-[(2R)-2-methyl-1-pyrrolidin-1-yl]-ethyl}-2-naphthalen-2-yl)-2H-pyridazin-3-one hydrobromide (Form I).

2-(6-{2-[(2R)-2-Methyl-1-pyrrolidin-1-yl]-ethyl}-2-naphthalen-2-yl)-2H-pyridazin-3-one hydrobromide (Form I) is a solid that can be identified by its powder X-ray diffraction pattern in accordance with the Brief Description of the Drawings (FIG. 5).

Characteristic two-theta angles of the powder X-ray diffraction pattern for 2-(6-{2-[(2R)-2-methyl-1-pyrrolidin-1-yl]-ethyl}-2-naphthalen-2-yl)-2H-pyridazin-3-one hydrobromide (Form I) are 6.3°±0.1°, 9.8°±0.1°, 11.2°±0.1°, 12.5°±0.1°, 13.7°±0.1°, 15.6°±0.1°, 16.6°±0.1°, 18.2°±0.1°, 18.8°±0.1°, 20.8°±0.1°, 22.0°±0.1°, 22.4°±0.1°, 24.3°±0.1°, and 25.3°±0.1°. The most characteristic two-theta angles in the X-ray diffraction pattern are 12.5°±0.1°, 15.6°±0.1°, 16.6°±0.1°, 18.2°±0.1°, and 20.8°±0.1°.

Figure 6:
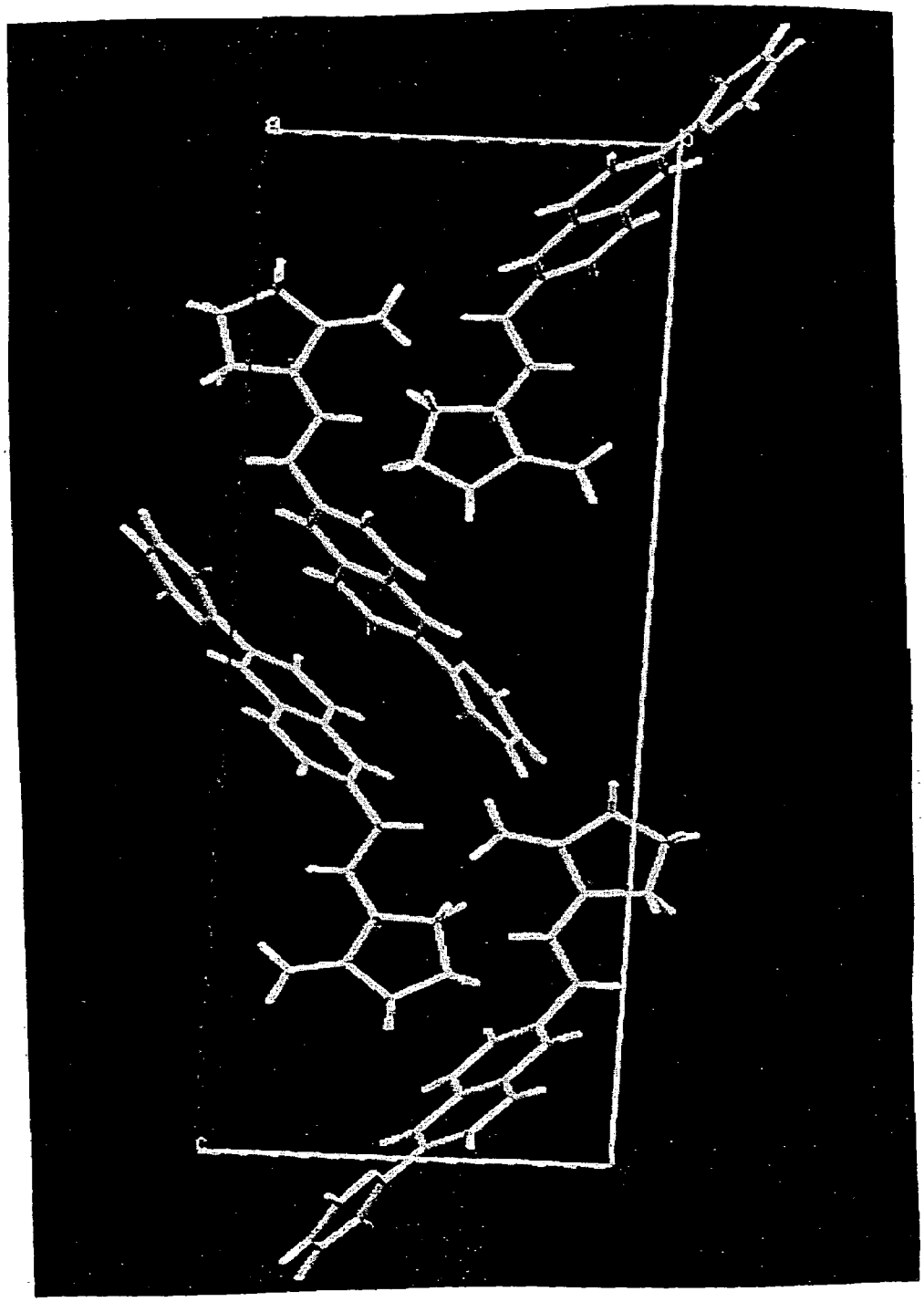
FIG. 6 depicts the crystal lattice arrangement of a 2-(6-{2-[(2R)-2-methyl-1-pyrrolidin-1-yl]-ethyl}-2-naphthalen-2-yl)-2H-pyridazin-3-one hydrobromide (Form I) unit cell.

The crystallographic unit cell parameters of a single salt of 2-(6-{2-[(2R)-2-methyl-1-pyrrolidin-1-yl]-ethyl}-2-naphthalen-2-yl)-2H-pyridazin-3-one hydrobromide (Form I) have been determined as having the following parameters a is 7.2357 (9) Å; b is 9.538 (1) Å; and c is 28.239 (4) Å to afford a cell volume of 1949.0 (4) Å$^3$, wherein a, b, and c are each a representative length of the crystal lattice. The hydrobromide salt (Form I) crystallizes in the orthorhombic space group $P2_12_12_1$. The crystal structure of 2-(6-{2-methyl-1-pyrrolidin-1-yl]-ethyl}-2-naphthalen-2-yl)-2H-pyridazin-3-one hydrobromide (Form I) is depicted in FIG. 6.

Figure 6A:
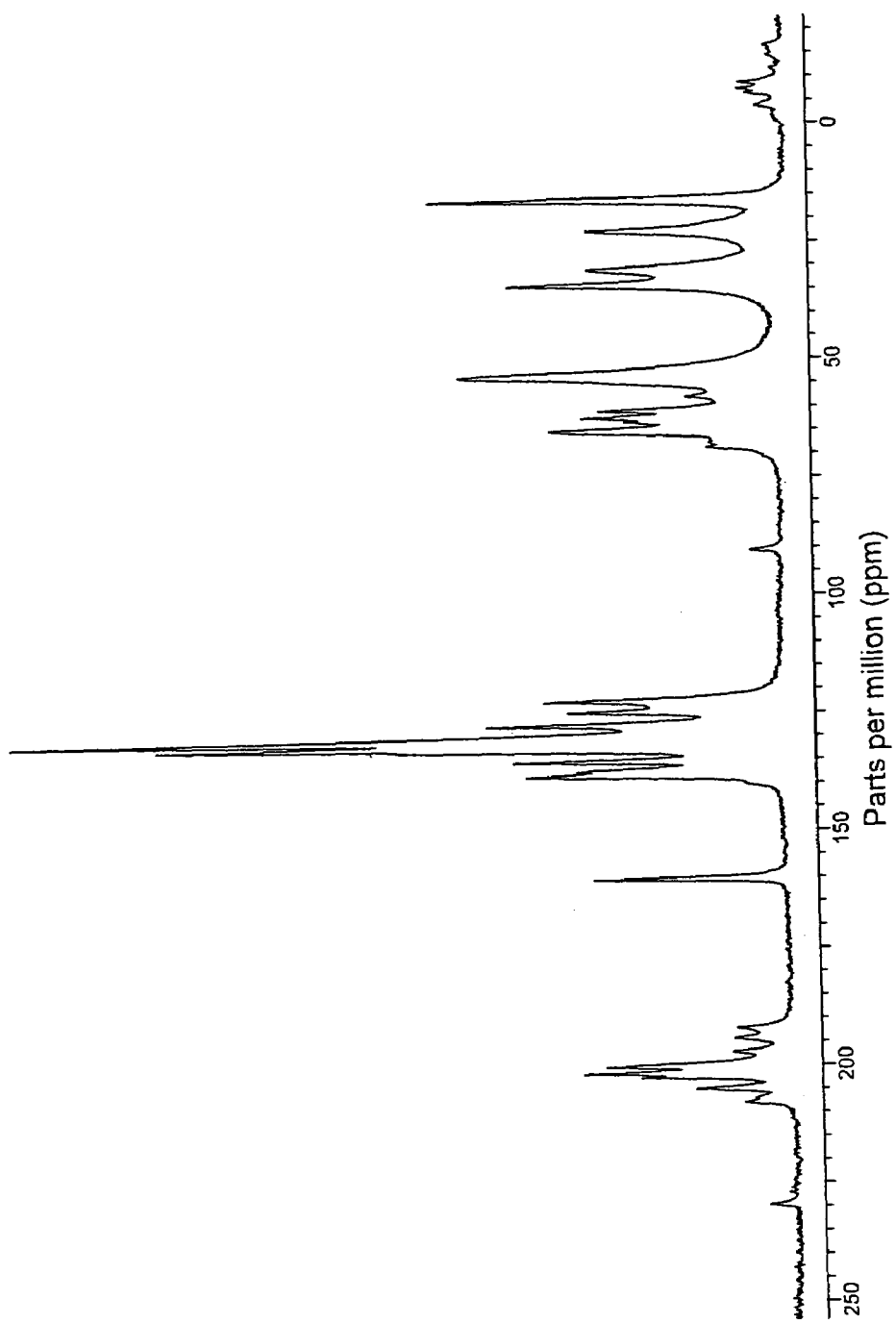
FIG. 6A is the solid state $^{13}$C NMR spectra of a 2-(6-{2-[(2R)-2-methyl-1-pyrrolidin-1-yl]-ethyl}-2-naphthalen-2-yl)-2H-pyridazin-3-one hydrobromide (Form I) unit cell.

Solid state $^{13}$Carbon NMR analysis demonstrates that 2-(6-{2-[(2R)-2-methyl-1-pyrrolidin-1-yl]-ethyl}-2-naphthalen-2-yl)-2H-pyridazin-3-one hydrobromide (Form I) shows characteristic $^{13}$C NMR at δ 160.1, 138.2, 137.2, 135.1, 132.6, 131.7, 130.3, 127.4, 124.6, 122.4, 65.0, 53.2, 34.1, 30.8, 22.6, and 15.9. The $^{13}$Carbon NMR spectrum is shown in FIG. 6A.

Figure 7:
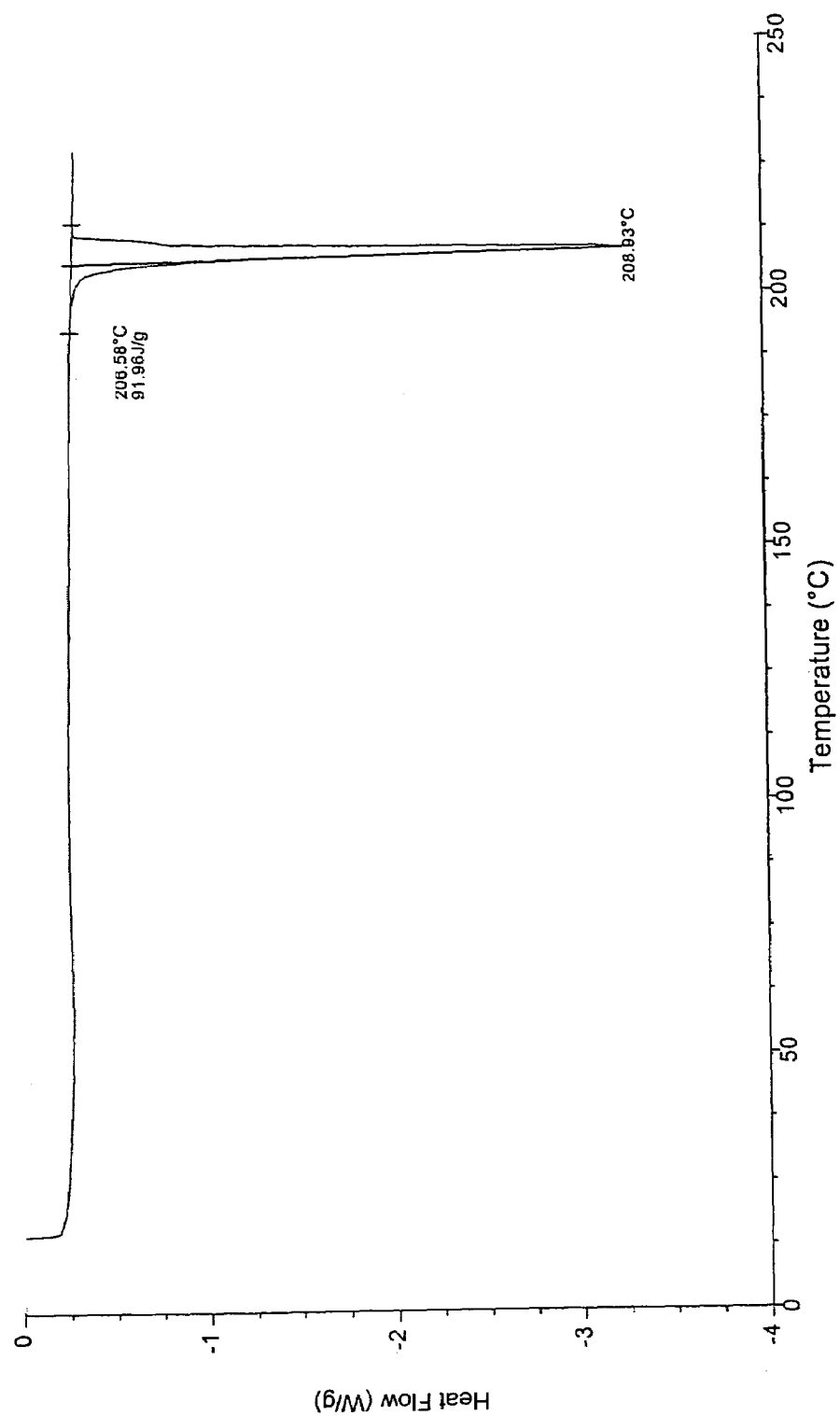
FIG. 7 is the differential scanning calorimetry thermogram of 2-(6-{2-[(2R)-2-methyl-1-pyrrolidin-1-yl]-ethyl}-2-naphthalen-2-yl)-2H-pyridazin-3-one hydrobromide (Form I).

Differential scanning calorimetry analysis confirms that the melting point of 2-(6-{2-[(2R)-2-methyl-1-pyrrolidin-1-yl]-ethyl}-2-naphthalen-2-yl)-2H-pyridazin-3-one hydrobromide (Form I) is 204° C.–210° C. (FIG. 7).

Figure 8:
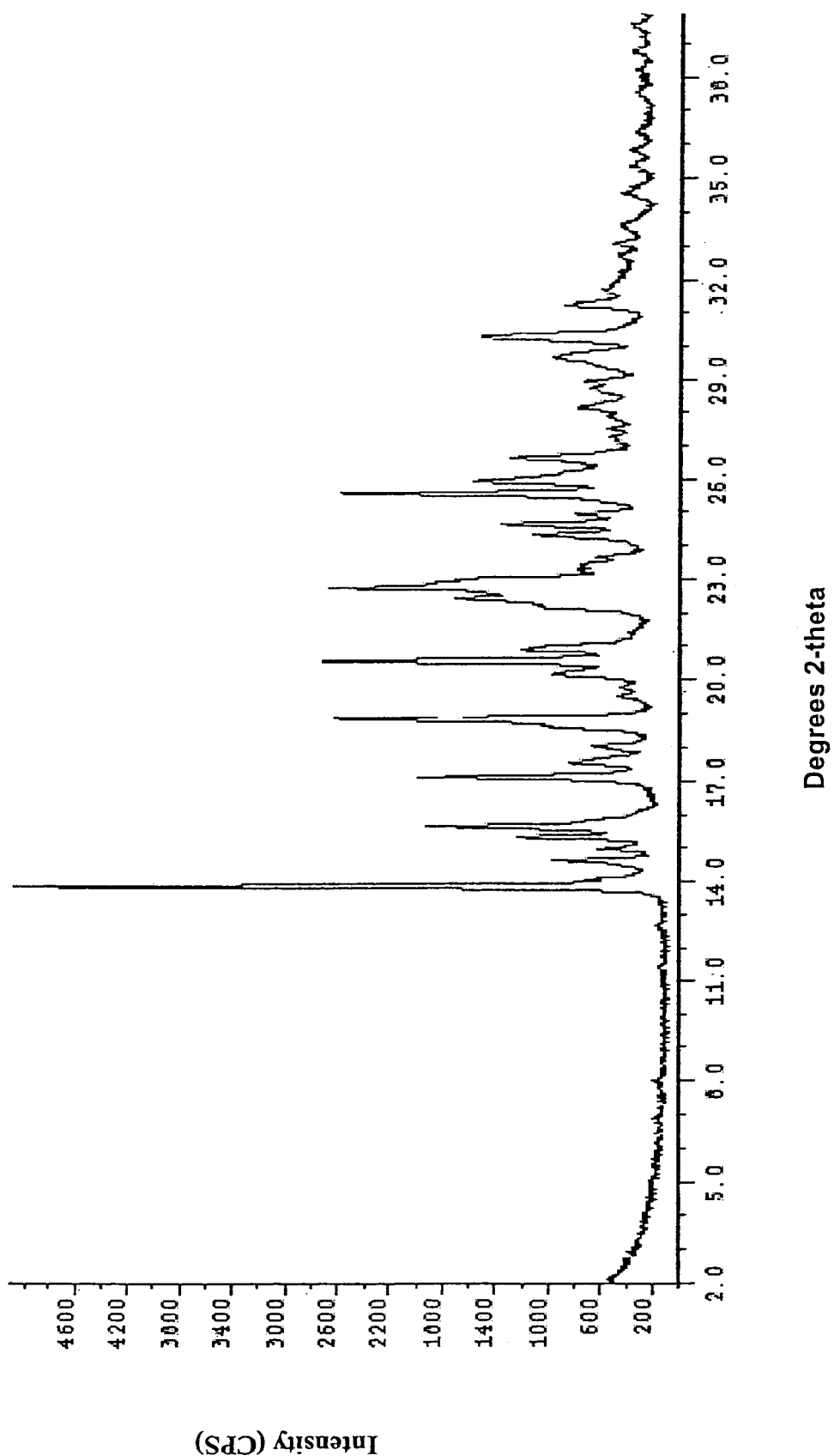
FIG. 8 is the powder X-ray diffractogram of 2-(6-{2-[(2R)-2-methyl-1-pyrrolidin-1-yl]-ethyl}-2-naphthalen-2-yl)-2H-pyridazin-3-one hydrobromide (Form II).
Figure 9:
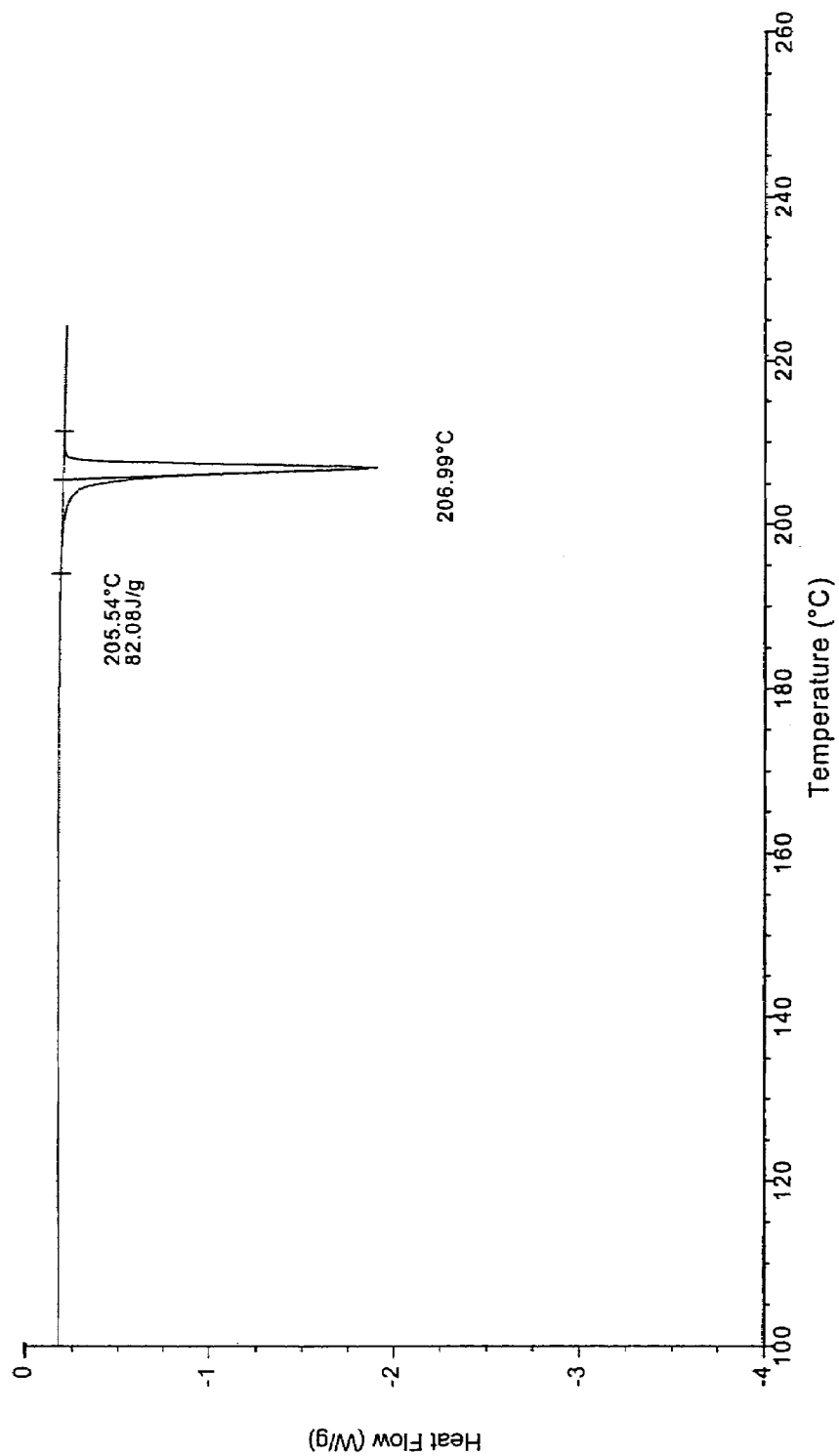
FIG. 9 is the differential scanning calorimetry thermogram of 2-(6-{2-[(2R)-2-methyl-1-pyrrolidin-1-yl]-ethyl}-2-naphthalen-2-yl)-2H-pyridazin-3-one hydrobromide (Form II).

The powder X-ray diffraction pattern of 2-(6-{2-[(2R)-2-methyl-1-pyrrolidin-1-yl]-ethyl}-2-naphthalen-2-yl)-2H-pyridazin-3-one hydrobromide (Form II) demonstrates characteristic 2-theta angles of: 13.884°±0.1°, 17.138°±0.1°, 18.860°±0.1°, 20.591°±0.1° and 25.584°±0.1° (FIG. 8). The melting point of 2-(6-{2-[(2R)-2-methyl-1-pyrrolidin-1-yl]-ethyl}-2-naphthalen-2-yl)-2H-pyridazin-3-one (Form II) as determined by DSC analysis is 206° C.–209° C. (FIG. 9).

Figure 10:
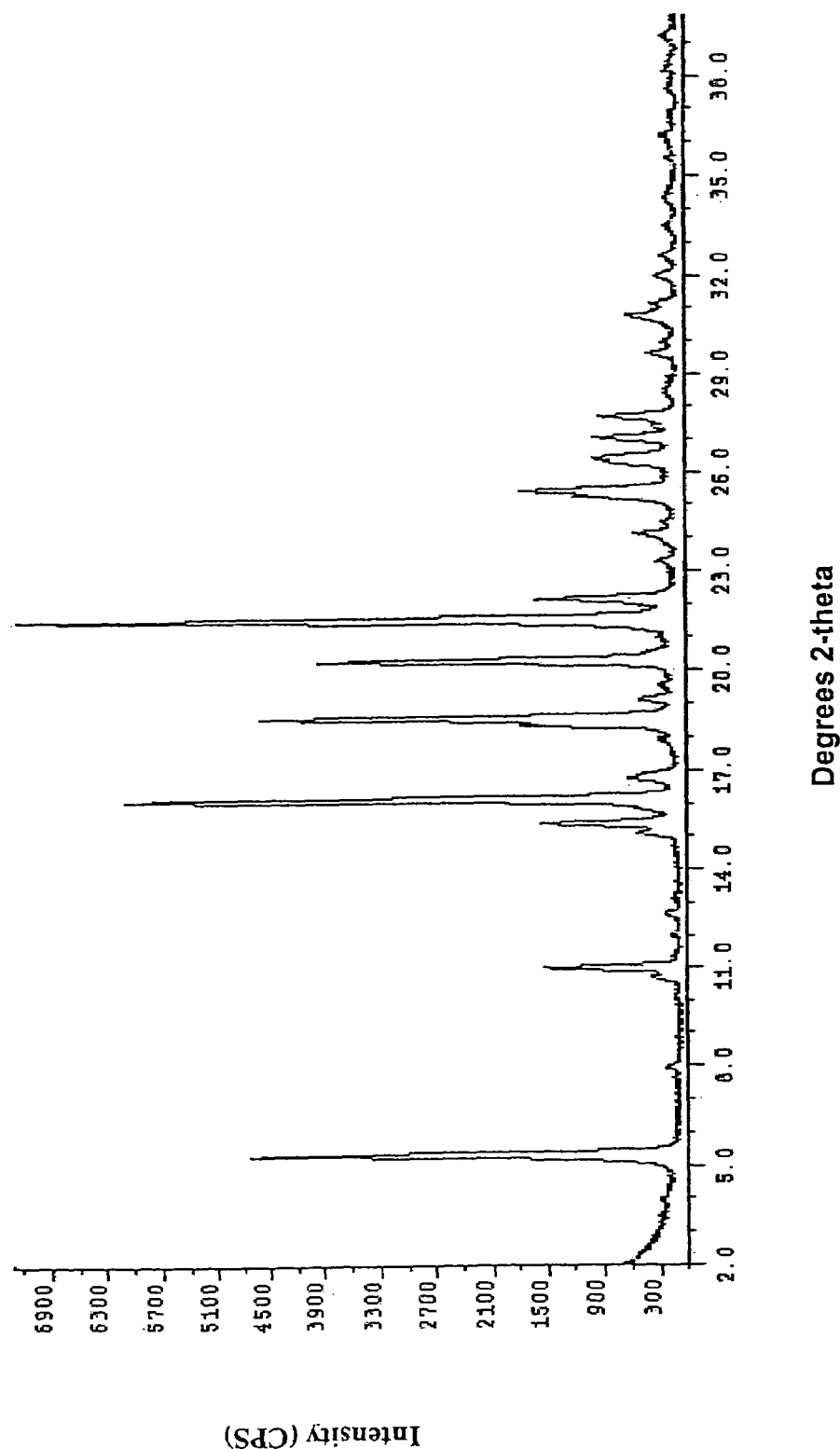
FIG. 10 is the powder X-ray diffractogram of 2-(6-{2-[(2R)-2-methyl-1-pyrrolidin-1-yl]-ethyl}-2-naphthalen-2-yl)-2H-pyridazin-3-one maleate.
Figure 11:
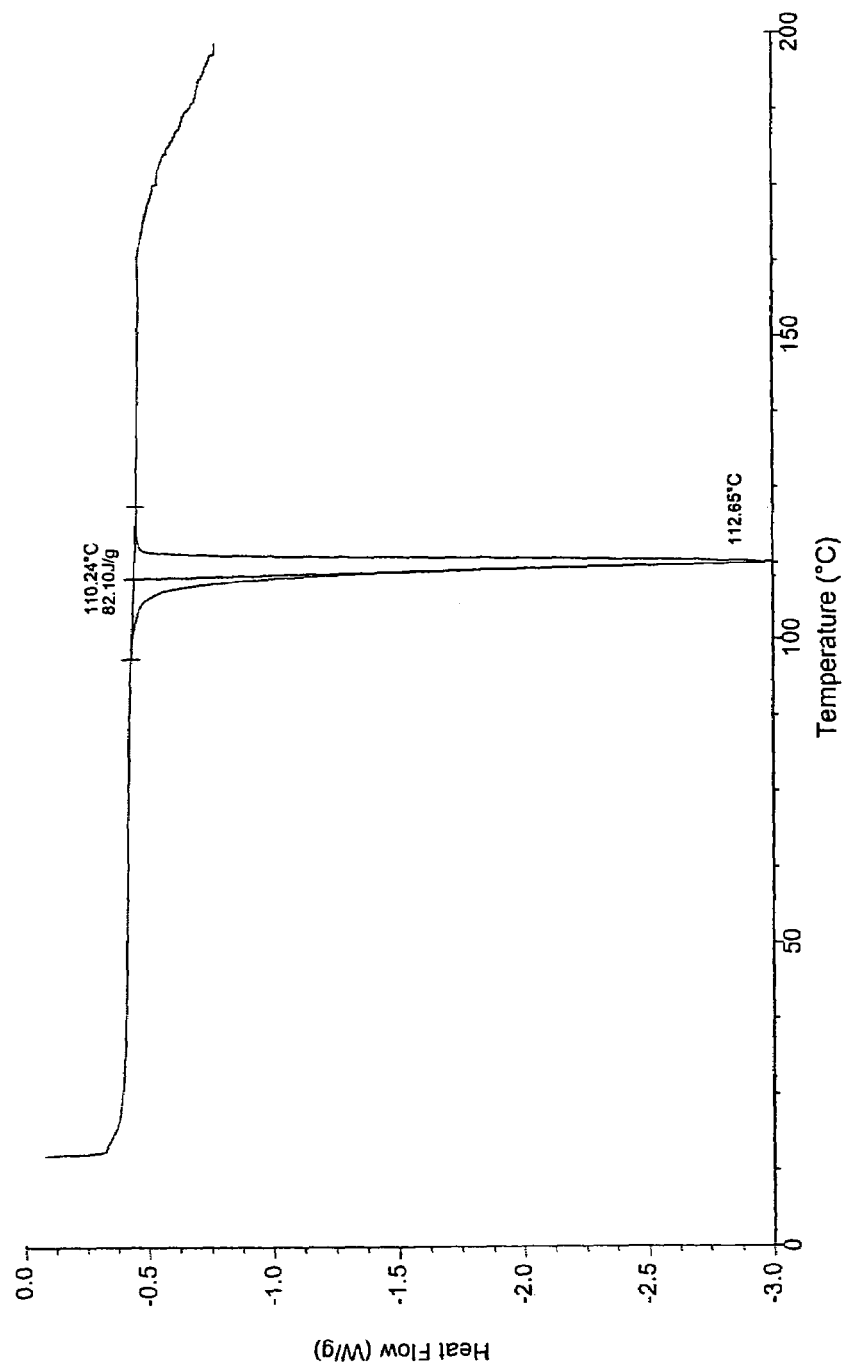
FIG. 11 is the differential scanning calorimetry thermogram of 2-(6-{2-[(2R)-2-methyl-1-pyrrolidin-1-yl]-ethyl}-2-naphthalen-2-yl)-2H-pyridazin-3-one maleate.

The powder X-ray diffraction pattern of 2-(6-{2-[(2R)-2-methyl-1-pyrrolidin-1-yl]-ethyl}-2-naphthalen-2-yl)-2H-pyridazin-3-one maleate demonstrates characteristic 2-theta angles of: 5.353°±0.1°, 11.017°±0.1°, 16.768°±0.1°, 15.576°±0.1° and 21.554°±0.1° (FIG. 10). The melting point of 2-(6-{2-[(2R)-2-methyl-1-pyrrolidin-1-yl]-ethyl}-2-naphthalen-2-yl)-2H-pyridazin-3-one maleate as determined by DSC analysis is 112° C.–114° C. (FIG. 11).

Figure 12:
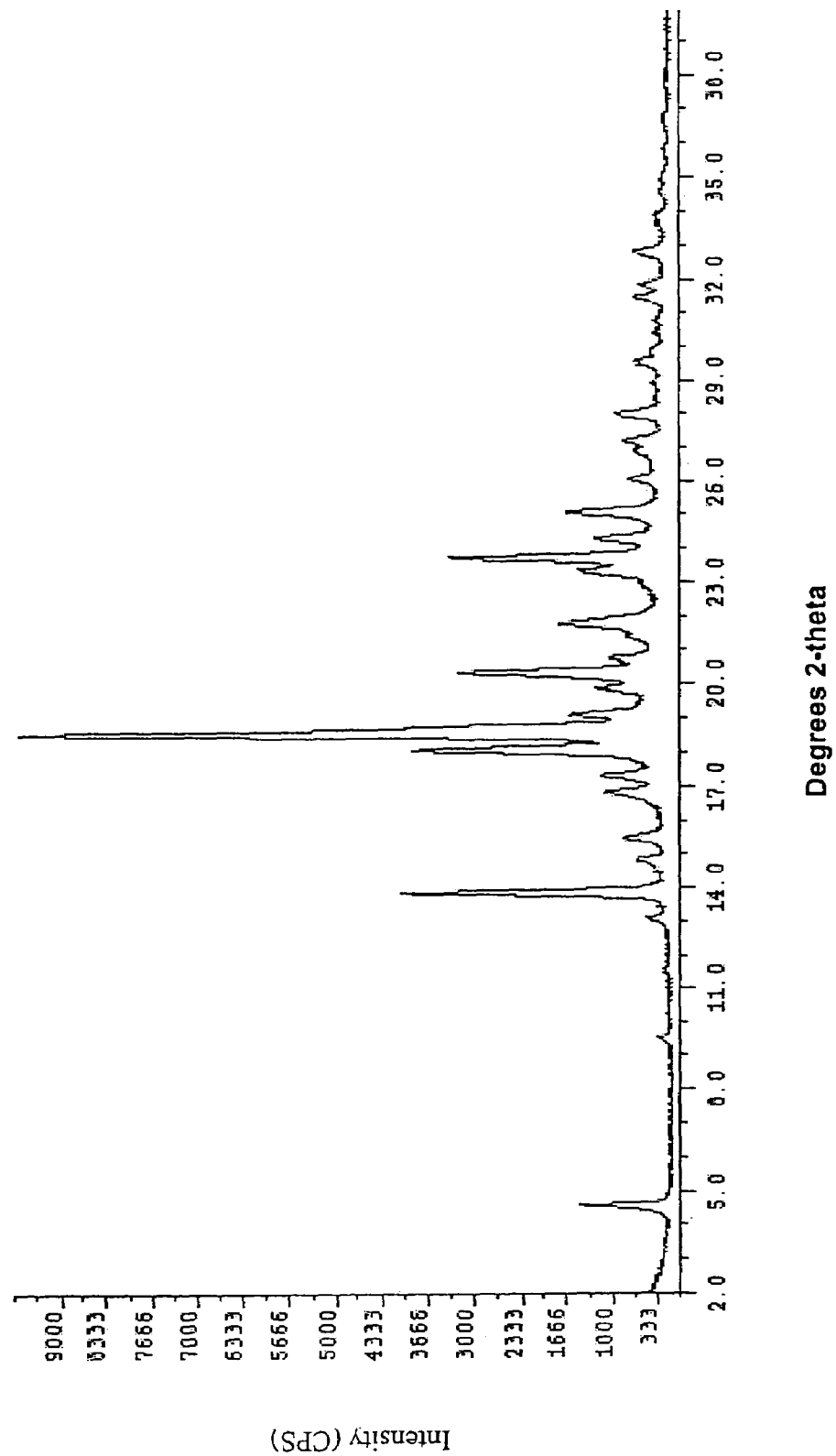
FIG. 12 is the powder X-ray diffractogram of 2-(6-{2-[(2R)-2-methyl-1-pyrrolidin-1-yl]-ethyl}-2-naphthalen-2-yl)-2H-pyridazin-3-one fumarate.
Figure 13:
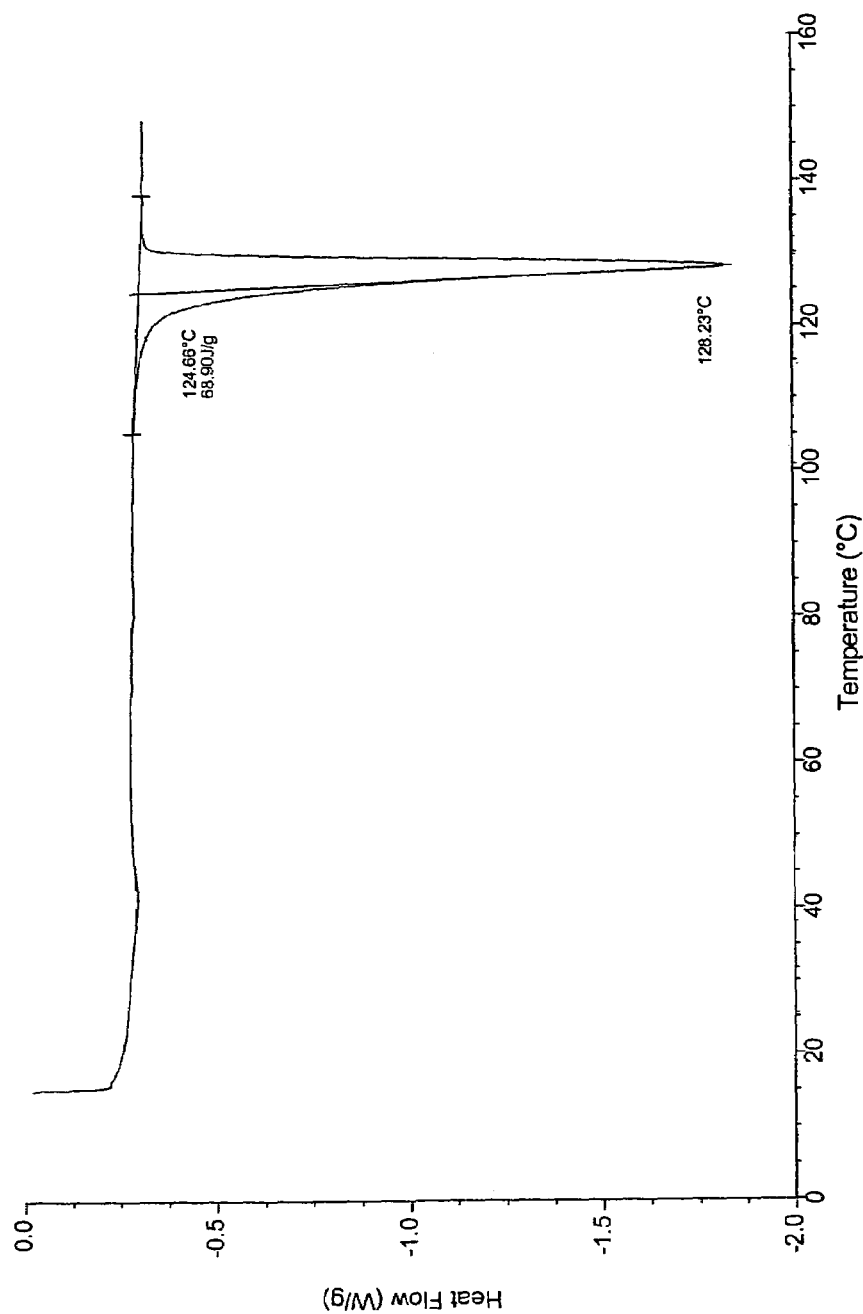
FIG. 13 is the differential scanning calorimetry thermogram of 2-(6-{2-[(2R)-2-methyl-1-pyrrolidin-1-yl]-ethyl}-2-naphthalen-2-yl)-2H-pyridazin-3-one fumarate.

The powder X-ray diffraction pattern of 2-(6-{2-[(2R)-2-methyl-1-pyrrolidin-1-yl]-ethyl}-2-naphthalen-2-yl)-2H-pyridazin-3-one fumarate demonstrates characteristic 2-theta angles of: 4.614°±0.1°, 13.881°±0.1°, 18.086°±0.1°, 18.580°±0.1° and 23.748°±0.1° (FIG. 12). The melting point of 2-(6-{2-[(2R)-2-methyl-1-pyrrolidin-1-yl]-ethyl}-2-naphthalen-2-yl)-2H-pyridazin-3-one fumarate as determined by DSC analysis is 126° C.–130° C. (FIG. 13).

Figure 14:
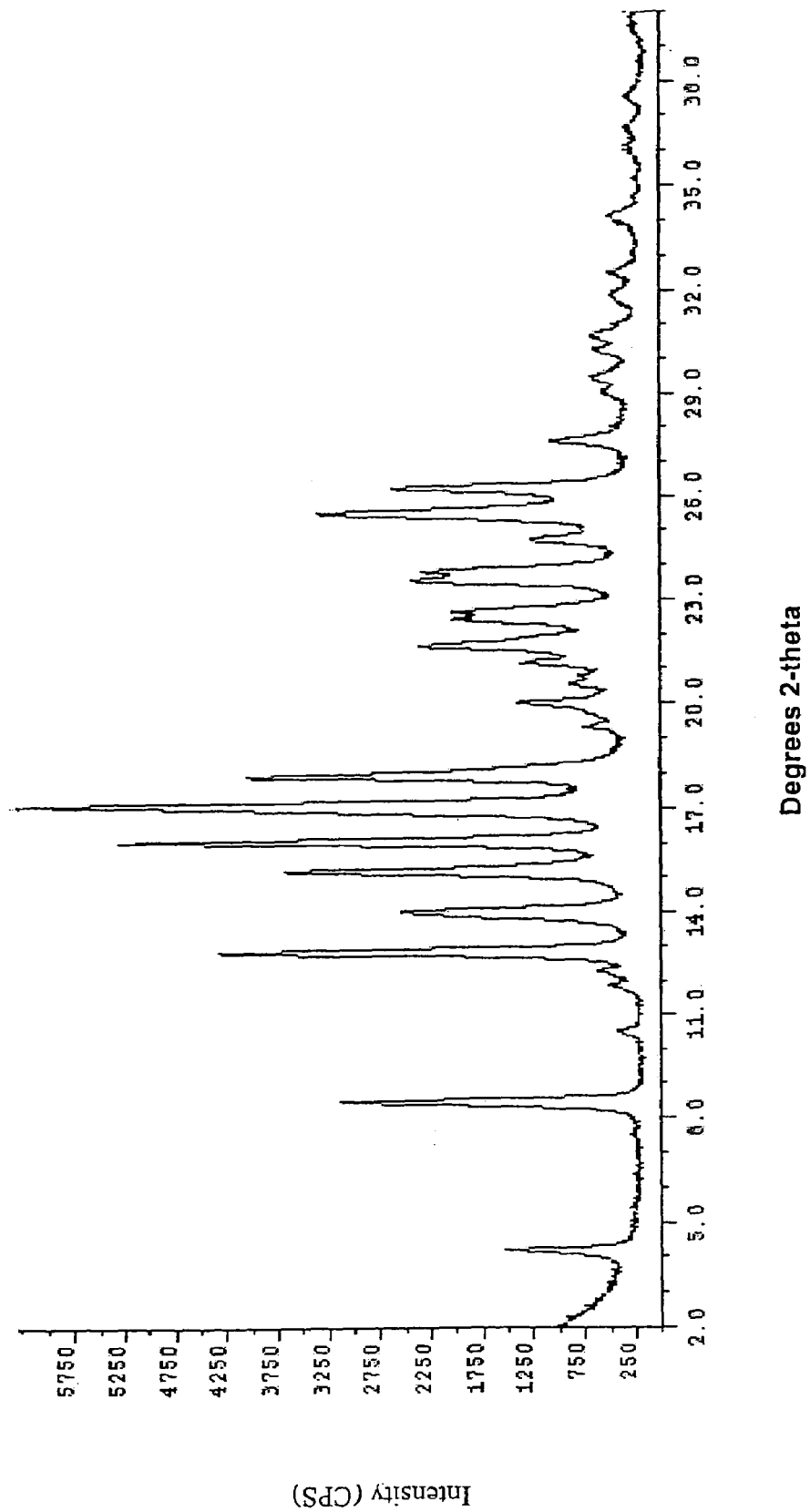
FIG. 14 is the powder X-ray diffractogram of 2-(6-{2-[(2R)-2-methyl-1-pyrrolidin-1-yl]-ethyl}-2-naphthalen-2-yl)-2H-pyridazin-3-one salicylate.
Figure 15:
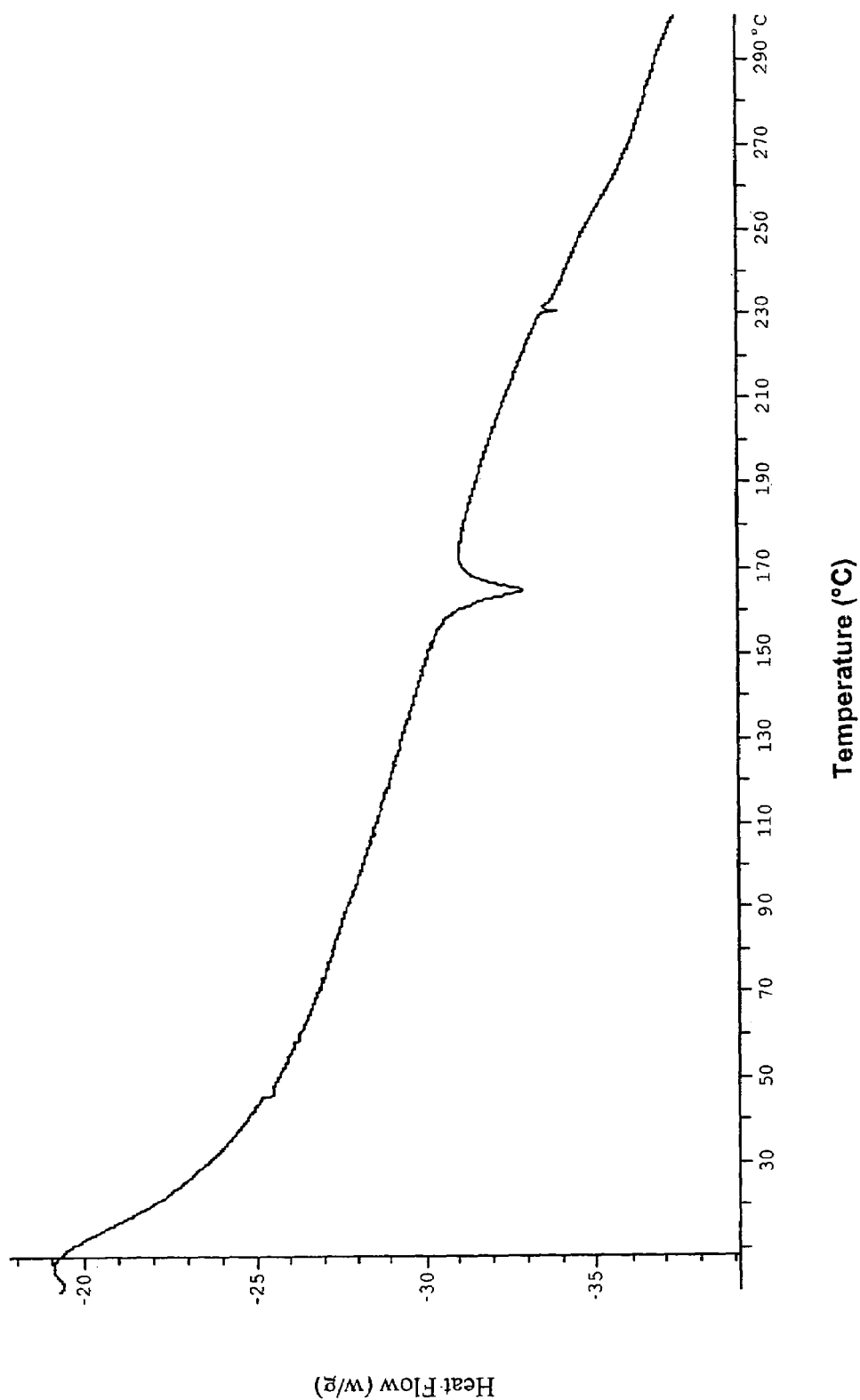
FIG. 15 is the differential scanning calorimetry thermogram of 2-(6-{2-[(2R)-2-methyl-1-pyrrolidin-1-yl]-ethyl}-2-naphthalen-2-yl)-2H-pyridazin-3-one salicylate.

The powder X-ray diffraction pattern of 2-(6-{2-[(2R)-2-methyl-1-pyrrolidin-1-yl]-ethyl}-2-naphthalen-2-yl)-2H-pyridazin-3-one salicylate demonstrates characteristic 2-theta angles of: 4.241°±0.1°, 8.516°±0.1°, 12.854°±0.1°, 14.030°±0.1° and 15.208°±0.1° (FIG. 14). The melting point of 2-(6-{2-[(2R)-2-methyl-1-pyrrolidin-1-yl]-ethyl}-2-naphthalen-2-yl)-2H-pyridazin-3-one salicylate as determined by DSC analysis is 163° C.–165° C. (FIG. 15).

Figure 16:
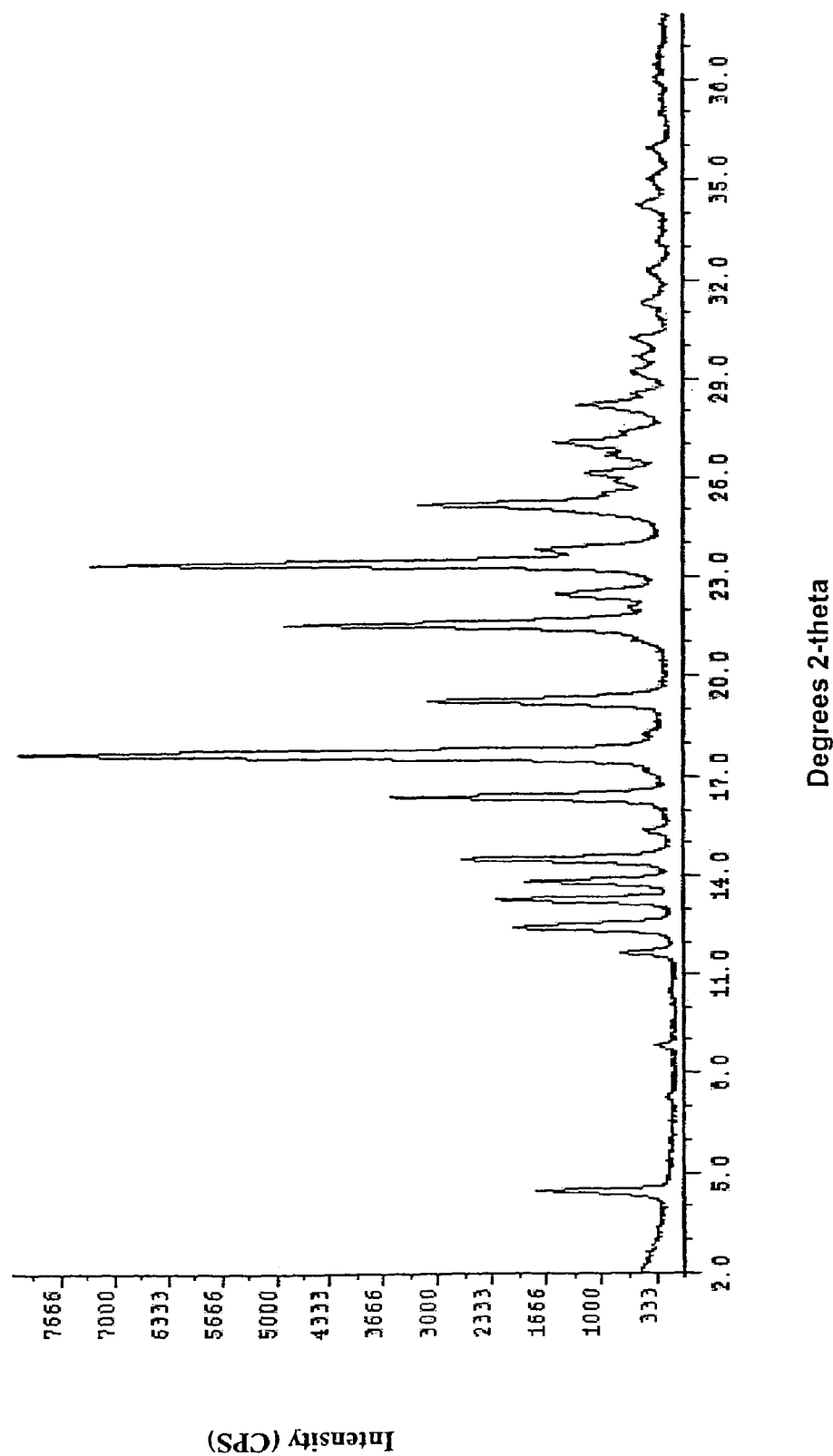
FIG. 16 is the powder X-ray diffractogram of 2-(6-{2-[(2R)-2-methyl-1-pyrrolidin-1-yl]-ethyl}-2-naphthalen-2-yl)-2H-pyridazin-3-one sulfate.
Figure 17:
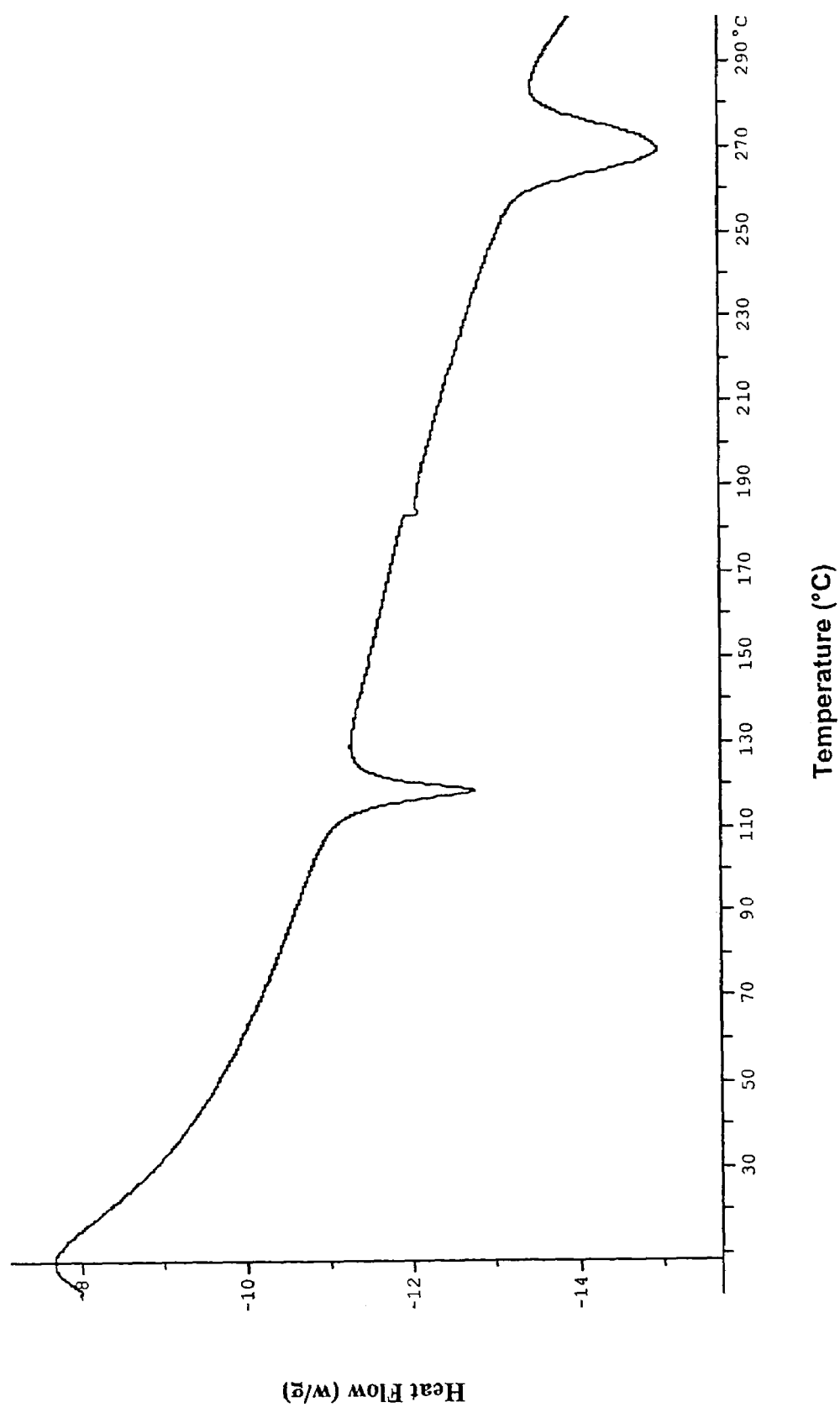
FIG. 17 is the differential scanning calorimetry thermogram of 2-(6-{2-[(2R)-2-methyl-1-pyrrolidin-1-yl]-ethyl}-2-naphthalen-2-yl)2H-pyridazin-3-one sulfate.

The powder X-ray diffraction pattern of 2-(6-{2-[(2R)-2-methyl-1-pyrrolidin-1-yl]-ethyl}-2-naphthalen-2-yl)-2H-pyridazin-3-one sulfate demonstrates characteristic 2-theta angles of: 12.447°±0.1°, 13.298°±0.1°, 14.521°±0.1°, 16.399°±0.1° and 17.718°±0.1° (FIG. 16). The melting point of 2-(6-{2-[(2R)-2-methyl-1-pyrrolidin-1-yl]-ethyl}-2- naphthalen-2-yl)-2H-pyridazin-3-one as determined by DSC analysis is 265° C.–268° C. (FIG. 17).

Figure 18:
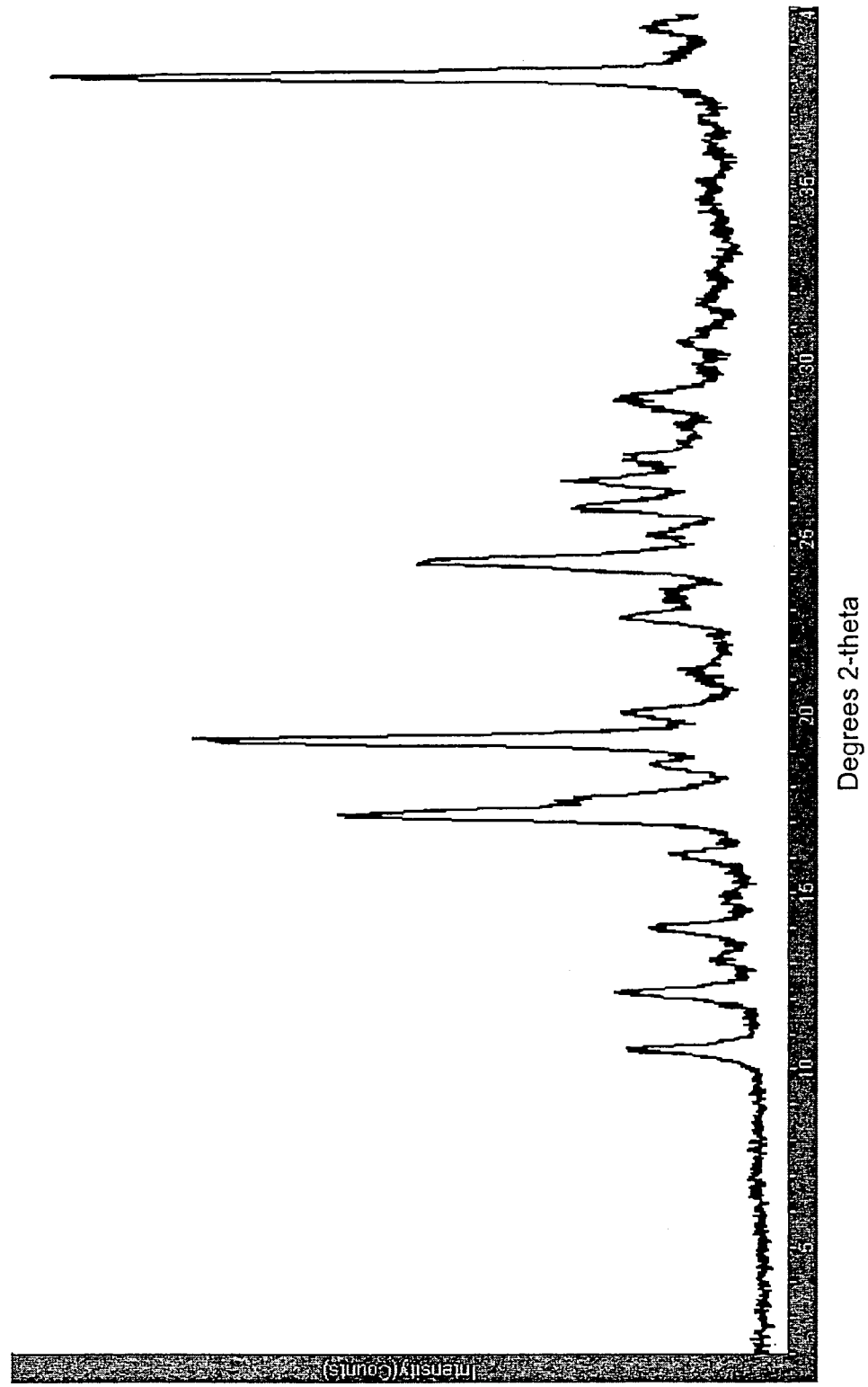
FIG. 18 is the powder X-ray diffractogram of 2-(6-{2-[(2R)-2-methyl-1-pyrrolidin-1-yl]-ethyl}-2-naphthalen-2-yl)-2H-pyridazin-3-one tosylate.
Figure 19:
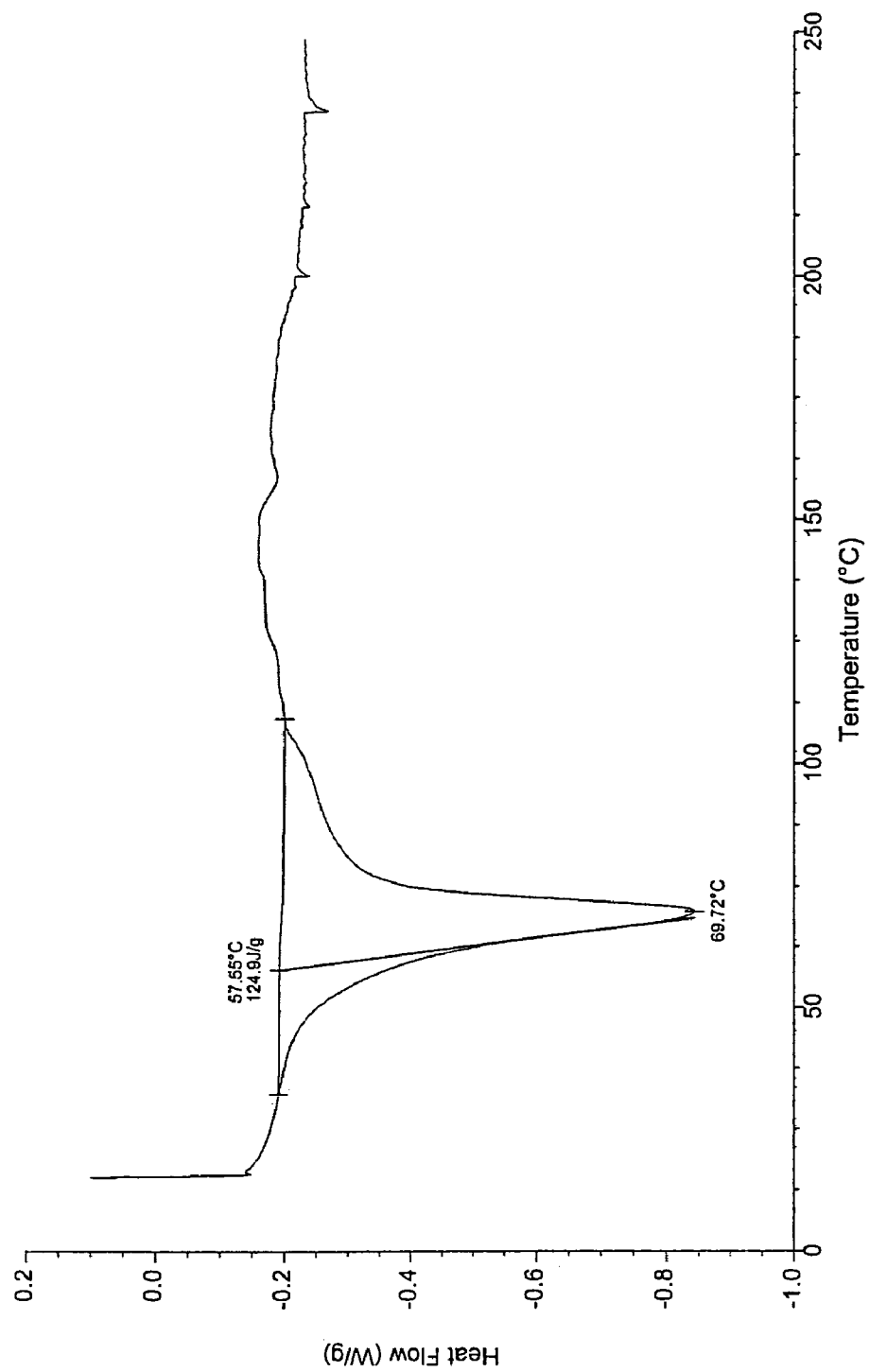
FIG. 19 is the differential scanning calorimetry thermogram of 2-(6-{2-[(2R)-2-methyl-1-pyrrolidin-1-yl]-ethyl}-2-naphthalen-2-yl)-2H-pyridazin-3-one tosylate.

The powder X-ray diffraction pattern of 2-(6-{2-[(2R)-2-methyl-1-pyrrolidin-1-yl]-ethyl}-2-naphthalen-2-yl)-2H-pyridazin-3-one tosylate demonstrates characteristic 2-theta angles of: 10.599°±0.1°, 12.179°±0.1°, 14.019°±0.1°, 17.240°±0.1° and 19.379°±0.1° (FIG. 18). The melting point of 2-(6-{2-[(2R)-2-methyl-1-pyrrolidin-1-yl]-ethyl}-2-naphthalen-2-yl)-2H-pyridazin-3-one tosylate as determined by DSC analysis is 58° C.–70° C. (FIG. 19).

As used herein, the term "substantially pure", when used in reference to a 2-(6-{2-[(2R)-2-methyl-1-pyrrolidin-1-yl]-ethyl}-2-naphthalen-2-yl)-2H-pyridazin-3-one salt, refers to that salt which is greater than about 90% pure. The crystalline form of 2-(6-{2-[(2R)-2-methyl-1-pyrrolidin-1-yl]-ethyl}-2-naphthalen-2-yl)-2H-pyridazin-3-one does not contain more than about 10% of any other compound and, in particular, does not contain more than about 10% of any other form of 2-(6-{2-[(2R)-2-methyl-1-pyrrolidin-1-yl]-ethyl}-2-naphthalen-2-yl)-2H-pyridazin-3-one, such as amorphous, solvated forms, non-solvated forms, and desolvated forms. More preferably, the term "substantially pure" refers to a 2-(6-{2-[(2R)-2-methyl-1-pyrrolidin-1-yl]-ethyl}-2-naphthalen-2-yl)-2H-pyridazin-3-one salt which is greater than about 95% pure. In such form, the 2-(6-{2-[(2R)-2-methyl-1-pyrrolidin-1-yl]-ethyl}-2-naphthalen-2-yl)-2H-pyridazin-3-one salt does not contain more than about 5% of any other compound and, in particular, any other form of 2-(6-{2-[(2R)-2-methyl-1-pyrrolidin-1-yl]-ethyl}-2-naphthalen-2-yl)-2H-pyridazin-3-one, such as amorphous, solvated forms, non-solvated forms, and desolvated forms. Even more preferably, the term "substantially pure" refers to a 2-(6-{2-[(2R)-2-methyl-1-pyrrolidin-1-yl]-ethyl}-2-naphthalen-2-yl)-2H-pyridazin-3-one salt which is greater than about 97% pure. In such salt, the 2-(6-{2-[(2R)-2-methyl-1-pyrrolidin-1-yl]-ethyl}-2-naphthalen-2-yl)-2H-pyridazin-3-one salt contains no more than 3% of any other compound and, in particular, does not contain more than 3% of any other form of 2-(6-{2-[(2R)-2-methyl-1-pyrrolidin-1-yl]-ethyl}-2-naphthalen-2-yl)-2H-pyridazin-3-one, such as amorphous, solvated forms, non-solvated forms, and desolvated forms.

Yet even more preferably, the term "substantially pure" refers to a 2-(6-{2-[(2R)-2-methyl-1-pyrrolidin-1-yl]-ethyl}-2-naphthalen-2-yl)-2H-pyridazin-3-one salt which is greater than about 99% pure. The 2-(6-{2-[(2R)-2-methyl-1-pyrrolidin-1-yl]-ethyl}-2-naphthalen-2-yl)-2H-pyridazin-3-one salt contains no more than about 1% of any other compound and, in particular, any other form of 2-(6-{2-[(2R)-2-methyl-1-pyrrolidin-1-yl]-ethyl}-2-naphthalen-2-yl)-2H-pyridazin-3-one, such as amorphous, solvated forms, non-solvated forms, and desolvated forms.

Powder X-ray diffraction (PXRD) analysis of samples was conducted in the following manner. Samples for X-ray diffraction analysis were prepared by spreading the sample powder (ground to a fine powder with mortar and pestle, or with glass microscope slides for limited quantity samples) in a thin layer on the sample holder and gently flattening the sample with a microscope slide. Samples were run in one of three configurations: circular bulk holder, a quartz zero background plate or hot stage mount (similar mounting to a zero background plate). X-ray powder diffraction was performed using a Rigaku Miniflex diffractometer (30 kV and 15 mA; X-ray source: Cu; Range: 2.00–40.00° Two Theta; Scan Rate: 5 degree/minute) or a Scintag X1 or X2 diffractometer (2 kW normal focus X-ray tube with either a liquid nitrogen or Peltier cooled germanium solid state detector; 45 kV and 40 mA; X-ray source: Cu; Range: 2.00–40.00° Two Theta; Scan Rate: 1 degree/minute).

Single Crystal X-ray diffraction analysis of samples was conducted in the following manner. Samples for X-ray diffraction analysis were prepared by affixing selected single crystals to glass pins with epoxy adhesive. X-ray diffraction data was collected using a Bruker SMART system with an APEX area detector (50 kV and 40 mA; X-ray source: Mo).

Characteristic powder X-ray diffraction pattern peak positions are reported for salts in terms of angular positions (two theta) with an allowable variability of ±0.1°. The allowable variability is specified in the U.S. Pharmacopeia, pages 1843–1844 (1995). The variability of ±0.1° is intended to be used when comparing two powder X-ray diffraction patterns. In practice, if a diffraction pattern peak from one pattern is assigned a range of angular positions (two theta) which is the measured peak position ±0.1° and a diffraction pattern peak from another pattern is assigned a range of angular positions (two theta) which is the measured peak position ±0.1° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.10°–5.30°. If a comparison peak from the other diffraction pattern is determined to have a peak position of assigned a position in the range of 5.25°–5.45°. Because there is overlap between the two ranges of peak positions (i.e., 5.10°–5.30° and 5.25°–5.45°) the two peaks being compared are considered to have the same angular position (two theta).

Nuclear magnetic resonance (NMR) analysis of samples was conducted in the following manner. A Bruker AMX-400 instrument was used with the following parameters: spectrometer frequency for $^1H$ was 400 MHz; spectrometer frequency for $^{13}C$ was 100 MHz.

Solid state $^{13}C$ nuclear magnetic resonance spectra were collected on a Bruker AMX-400 spectrometer using a 7 mm CPMAS probe operating at a spectrometer frequency of 100.628 MHz. The sample was spun at 7 kHz and the data was collected using the Variable Amplituded CP2LEV pulse sequence with a 15 millisecond contact time.

Differential scanning calorimetric (DSC) analysis of samples was conducted in the following manner. A.T.A. Instruments Model Q1000 differential scanning calorimeter with a Mettler 821 DSC cell using standard software to identify the onset of the melt. The analysis parameters were: sample weight 1–2 mg, placed in an aluminum pan, and sealed after a pin hole was poked in the lid; heating rate: 10° C./minute).

Mass spectroscopy (MS) analysis of samples was conducted using a Finnigan DCI/MS SSQ7000 instrument with a Zymark sample prep system.

Preparation of Compounds of the Invention

The compounds of the invention can be prepared from 2-(6-{2-[(2R)-2-methyl-1-pyrrolidin-1-yl]-ethyl}-2-naphthalen-2-yl)-2H-pyridazin-3-one, which is prepared by using any method that provides a stable, 2-(6-{2-[(2R)-2-methyl-1-pyrrolidin-1-yl]-ethyl}-2-naphthalen-2-yl)-2H-pyridazin-3-one compound, for example as described in U.S. patent application Ser. No. 10/689,735, filed on Oct. 22, 2003, or according to the general process as shown in Scheme 1.

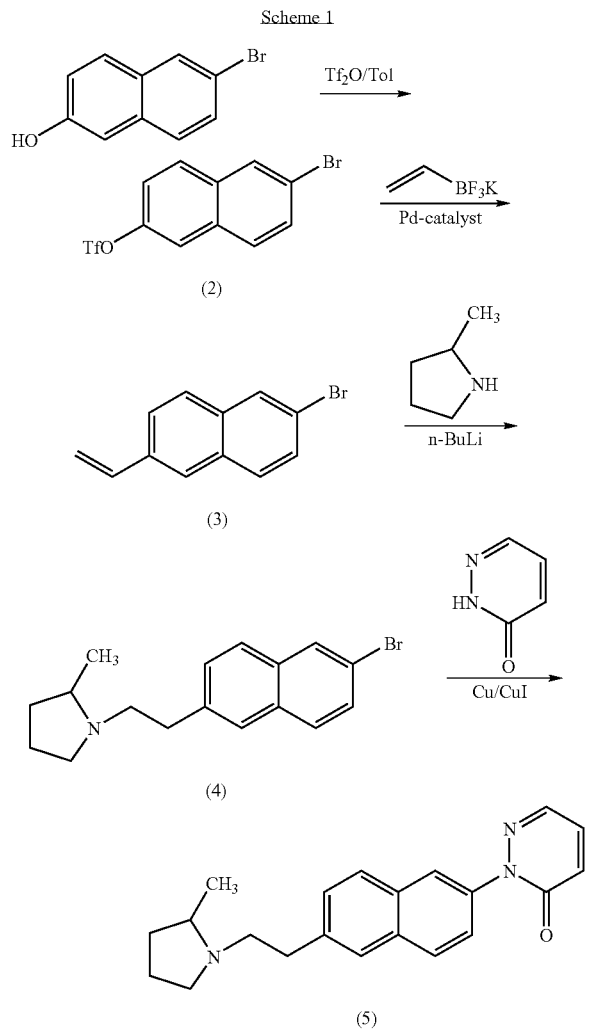

One process for the preparation of 2-{6-[2-(2-methyl-pyrrolidin-1-yl)-ethyl]-naphthalen-2-yl}-2H-pyridazin-3-one, which demonstrates activity as a histamine-3 receptor ligand, involves treating an inexpensive and readily available starting material, 6-bromo-naphthalen-2-ol, to afford 2-{6-[2-(2-methyl-pyrrolidin-1-yl)-ethyl]-naphthalen-2-yl}-2H-pyridazin-3-one. Briefly, the process involves providing 6-bromo-naphthalen-2-ol. Preparing the triflate, or trifluoromethansulfonic acid ester, of 6-bromo-naphthalen-2-ol (2) with trifluoromethanesulfonic anhydride or another suitable trifluoromethanesulfonic reagent. The resulting trifluoro-methanesulfonic acid 6-bromo-naphthalen-2-yl ester (2) is converted to 2-bromo-6-vinyl-naphthalene (3) via a Pd-catalyzed Suzuki cross-coupling reaction. The 2-bromo-6-vinyl-naphthalene is reacted with a 2-methylpyrrolidine anion generated with n-butyllithium to provide 1-[2-(6-bromo-naphthalen-2-yl)-ethyl]-2-methyl-pyrrolidine (4). Compound (4) is reacted with 2H-pyridazin-3-one to provide the desired 2-{6-[2-(2-methyl-pyrrolidin-1-yl)-ethyl]-naphthalen-2-yl}-2H-pyridazin-3-one (5).

The 6-bromo-naphthalen-2-ol can be treated with any suitable trifluoromethanesulfonic reagent in the presence of an organic base to provide a trifluoro-methanesulfonic acid 6-bromo-naphthalen-2-yl ester. Examples of suitable trifluoromethanesulfonic reagents are, for example, trifluoromethanesulfonyl acid anhydride, trifluoromethanesulfonyl chloride, N-phenyltrifluoromethanesulfonimide, trifluoromethanesulfonyl-1-H-imidazole, trifluoromethanesulfonyl acid anilide, trifluoromethanesulfony acid-2-nitrophenyl ester, trifluoromethanesulfonyl acid-4-nitrophenyl ester. Examples of organic base are, for example, triethylamine, diisopropylamine, diisopropylethylamine, 2,6-lutidine, pyridine, and 2,4-diaminobutyric acid (DBU).

The reaction can be accomplished in any suitable organic solvent. Examples of suitable solvents are $CH_2Cl_2$, dimethyl ether (DME), and toluene. The reaction also can be carried out in a biphasic condition where an inorganic base is used. For example, suitable inorganic base are $K_3PO_4$, $NaHCO_3$, $Na_2CO_3$, NaOH, and the like. The preferred solvent is toluene. Typically, the reacion is accomplished in biphasic conditions, for example use of toluene and 30% potassium phosphate, at low temperatures. The preferred temperature range for the reaction is from about $-5°$ C. to about $0°$ C.

The trifluoro-methanesulfonic acid 6-bromo-naphthalen-2-yl ester is converted to 2-bromo-6-vinyl-naphthalene via reaction with a vinyltrifluoroborate reagent. Suitable vinyl-trifluoroborate reagents are, for example, potassium vinyl-triflurorborate, 2-vinyl-4,4,5,5-tetramethyl-1,3,2-dioxaborolane, dibutyl vinylboronate. The reagent is used in an amount of from about 1.0 molar equivalent to about 1.5 molar equivalents relative to the trifluoro-methanesulfonic acid 6-bromo-naphthalen-2-yl ester. Typically, the reaction is carried out in a polar organic solvent, for example an alcohol, and a basic solution, for example a metal carbonate solution. A preferred solvent is ethanol. Examples of other solvents that can be used for the reaction are n-propanol, iso-propanol, methanol, and other suitable alcohols. The metal carbonate preferably is cesium carbonate. Alternatively, other metal carbonates, for example $Na_2CO_3$ and $K_3PO_4$ also can be used. The amount of metal carbonate for the reaction is from about 2 molar equivalents to about 4 molar equivalents relative to the trifluoro-methanesulfonic acid 6-bromo-naphthalen-2-yl ester. The reaction is accomplished in the presence of a palladium catalyst and an organic amino base, for example, such as triethylamine, diisopropylamine, and the like. Examples of palladium catalysts for the reaction include, but are not limited to, tetrakis(triphenylphosphine)palladium, $PdCl_2(dppf)_2$, $PdCl_2(Ph_3P)_2$, and $PdCl_2(CH_3CN)_2$. The preferred palladium catalyst is tetrakis(triphenylphosphine)palladium.

2-Bromo-6-vinyl-naphthalene is treated with a 2-methylpyrrolidine anion generated with n-butyllithium to provide 1-[2-(6-bromo-naphthalen-2-yl)-ethyl]-2-methyl-pyrrolidine. Preferably, about 1.2 to about 2.5 molar equivalents of 2-methylpyrrolidine are used for the reaction. The reaction typically is accomplished in an organic solvent, for example, THF, methyl-t-butyl ether (MTBE), $Et_2O$, and DME. The preferred solvent is tetrahydrofuran (THF). The n-butyllithium is added to a THF solution of 2-methylpyrrolidine in a controlled fashion, typically in a dropwise manner. To this solution is added a THF solution of 2-bromo-6-vinyl-naphthalene. Alternatively, it is also suitable to the THF solution of 2-bromo-6-vinyl-naphthalene to the solution of 2-methylpyrrolidine and n-butyllithium. The reaction is accomplished at below room temperature, typically in a temperature range from about $0°$ C. to about $-20°$ C. From about 0.3 to about 0.7 molar equivalents of n-butyllithium are used relative to the 2-bromo-6-vinylnaphthalene compound. The resulting compound is 1-[2-(6-bromo-naphthalen-2-yl)-ethyl]-2-methyl-pyrrolidine.

The 1-[2-(6-bromo-naphthalen-2-yl)-ethyl]-2-methyl-pyrrolidine is reacted with 2H-pyridazin-3-one to provide a desired 2-{6-[2-(2-methyl-pyrrolidin-1-yl)-ethyl]-naphthalen-2-yl}-2H-pyridazin-3-one compound, which can be further processed to prepare a suitable salt. The reaction is accomplished using 2H-pyridazin-3-one, 8-hydroxyquinoline, a copper catalyst in the presence of base. From about 1.0 to about 1.5 molar equivalents of (2H)-pyridazin-3-one are used relative to 1-[2-(6-bromo-naphthalen-2-yl)-2-methyl-pyrrolidine. The copper catalyst can be any suitable copper catalyst, for example copper (I) catalysts. Examples of suitable catalysts for the reaction include but are not limited to copper (0) powder, copper (I) chloride, copper (I) bromide, copper (I) iodide, copper (I) oxide, copper (I) acetate, copper (II) chloride, copper (II) bromide, copper (II) iodide, copper (II) oxide, copper (II) acetate copper. The preferred copper catalyst is copper (I) chloride. About 0.02 to about 1.0 molar equivalents of copper catalyst are used relative to the 1-[2-(6-bromo-naphthalen-2-yl)-ethyl]-2-methyl-pyrrolidine compound. Examples of suitable ligands for the reaction include, but are not limited to p-dimethylaminopyridine, pyridine, 3-picoline, 4-picoline, 8-hydroxyquinoline, 7-methyl-8-hydroxyquinoline, 7-n-propyl-8-hydroxyquinoline, 1,10-phenanthroline, and 2,2'-dipyridyl. The preferred ligand is 8-hydroxyquinoline, which is used in an amount of from about 0.02 to about 2.0 molar equivalents relative to 1-[2-(6-bromo-naphthalen-2-yl)-ethyl]-2-methyl-pyrrolidine. Preferably, the base is a metal carbonate or a metal alkoxide, for example cesium carbonate, potassium carbonate, sodium carbonate, and sodium tert-butoxide. The preferred base is potassium carbonate, which is used in an amount of from about 1.0 to about 2.0 molar equivalents relative to 1-[2-(6-bromo-naphthalen-2-yl)-ethyl]-2-methyl-pyrrolidine. The reaction is accomplished at elevated temperatures in a polar organic solvent. Examples of suitable solvents include but are not limited to N,N'-dimethylformamide, N-methylpyrrolidinone, N,N'-dimethylacetamide, pyridine, 3-picoline, 4-picoline, and the like. The preferred solvent is dimethylformamide (DMF). Typically, the reaction is accomplished under a nitrogen atmosphere, and the reaction mixture is heated to temperatures of from about 100° C. to about 160° C. The reaction typically can be accomplished in about 10 to about 48 hours. When the reaction is completed and cooled to 25° C., a non-water miscible solvent, for example ethyl acetate, is added. The organic solution is washed with a brine aqueous solution, for example 25% NaCl solution or other suitable salt solution several times. The organic solution is dried, and concentrated to dryness to give the product.

Alternatively, the 2-{6-[2-(2-methyl-pyrrolidin-1-yl)-ethyl]-naphthalen-2-yl}-2H-pyridazin-3-one, and more particularly 2-(6-{2-[(2R)-2-methyl-1-pyrrolidin-1-yl]-ethyl}-2-naphthalen-2-yl)-2H-pyridazin-3-one, active agent can be prepared according to procedures described in U.S. patent application Ser. No. 10/689,735, filed on Oct. 22, 2003, at least in, for example, the general procedures and Example 31, or any other suitable procedure for providing a stable active agent. Briefly, for example, a 6-bromo-2-naphthoate is reduced using $BH_3$-THF to provide the corresponding alcohol. 6-Bromo-naphthalen-2-yl)-methanol is treated with 3(2H)-pyridazinone, copper powder, and base to provide 2-[6-(2-hydroxy-ethyl)-naphthalen-2-yl]-2H-pyridazin-3-one, which is activated with a sulfonate, such as tosylate, and the sulfonate reacted with 2-methylpyrrolidine to afford 2-(6-{2-methyl-1-pyrrolidin-1-yl]-ethyl}-2-naphthalen-2-yl)-2H-pyridazin-3-one.

Salts of 2-{6-[2-(2-methyl-pyrrolidin-1-yl)-ethyl]-naphthalen-2-yl}-2H-pyridazin-3-one can be prepared from the active agent. More particularly, salts of 2-(6-{2-[(2 R)-2-methyl-1-pyrrolidin-1-yl]-ethyl}-2-naphthalen-2-yl)-2H-pyridazin-3-one can be prepared by mixing a solution of the anionic acid, in an amount of from about 1 to about 5 molar equivalents, in a suitable solvent to the 2-(6-{2-[(2R)-2-methyl-1-pyrrolidin-1-yl]-ethyl}-2-naphthalen-2-yl)-2H-pyridazin-3-one active agent in a suitable solvent. Typically, from about 5 L/kg to about 20 L/kg of the total suitable solvent is used. The resulting solution is heated to a desired temperature wherein any solids are dissolved in the solvent. The salt precipitates from the solution during slow cooling is filtered at ambient temperature.

The 2-(6-{2-[(2R)-2-methyl-1-pyrrolidin-1-yl]-ethyl}-2-naphthalen-2-yl)-2H-pyridazin-3-one citrate salt is prepared by mixing 2-(6-{2-[(2R)-2-methyl-1-pyrrolidin-1-yl]-ethyl}-2-naphthalen-2-yl)-2H-pyridazin-3-one with a suitable amount of citric acid solution. The citric acid solution contains a suitable amount of citric acid in an alcohol solvent, preferably ethanol. Typically, the amount of citric acid is from about 2 to about 5 molar equivalents relative to the 2-(6-{2-[(2R)-2-methyl-1-pyrrolidin-1-yl]-ethyl}-2-naphthalen-2-yl)-2H-pyridazin-3-one. The total volume used to dissolve citric acid is about 10 L/kg to about 20 L/kg of ethanol. The 2-(6-{2-[(2R)-2-methyl-1-pyrrolidin-1-yl]-ethyl}-2-naphthalen-2-yl)-2H-pyridazin-3-one can be mixed with the citric acid solution at, preferably, ambient temperature. The resulting solution is heated to dissolve the 2-(6-{2-[(2R)-2-methyl-1-pyrrolidin-1-yl]-ethyl}-2-naphthalen-2-yl)-2H-pyridazin-3-one. The reaction temperature of the solution is from about 30° C. to about 60° C.

A seed slurry of 2-(6-{2-[(2R)-2-methyl-1-pyrrolidin-1-yl]-ethyl}-2-naphthalen-2-yl)-2H-pyridazin-3-one citrate salt crystals in ethanol is added to the heated citric acid solution comprising 2-(6-{2-[(2R)-2-methyl-1-pyrrolidin-1-yl]-ethyl}-2-naphthalen-2-yl)-2H-pyridazin-3-one. Typically, seed crystals, for example salt from a previous preparation, are provided in a slurry of 2-(6-{2-[(2R)-2-methyl-1-pyrrolidin-1-yl]-ethyl}-2-naphthalen-2-yl)-2H-pyridazin-3-one citrate salt in ethanol solvent. The amount of 2-(6-{2-[(2R)-2-methyl-1-pyrrolidin-1-yl]-ethyl}-2-naphthalen-2-yl)-2H-pyridazin-3-one can range from about 1% to about 5% weight/weight relative to the 2-(6-{2-[(2R)-2-methyl-1-pyrrolidin-1-yl]-ethyl}-2-naphthalen-2-yl)-2H-pyridazin-3-one. The ethanol used for providing the slurry can be from about 10 mL/g to about 20 mL/g relative to the 2-(6-{2-[(2R)-2-methyl-1-pyrrolidin-1-yl]-ethyl}-2-naphthalen-2-yl)-2H-pyridazin-3-one citrate salt.

The resulting suspension of 2-(6-{2-[(2R)-2-methyl-1-pyrrolidin-1-yl]-ethyl}-2-naphthalen-2-yl)-2H-pyridazin-3-one, citric acid solution, and seed slurry can be carefully treated via heating and cooling to provide a more suitable suspension for filtering. For the sake of convenience, the resulting suspension is referred to as the "2-(6-{2-[(2R)-2-methyl-1-pyrrolidin-1-yl]-ethyl}-2-naphthalen-2-yl)-2H-pyridazin-3-one citrate suspension". The 2-(6-{2-[(2R)-2-methyl-1-pyrrolidin-1-yl]-ethyl}-2-naphthalen-2-yl)-2H-pyridazin-3-one citrate suspension is heated to a temperature of from about 40° C. to about 65° C. for at least 1 hour. Preferably, the suspension is heated for about 2 to 4 hours. The 2-(6-{2-[(2R)-2-methyl-1-pyrrolidin-1-yl]-ethyl}-2-naphthalen-2-yl)-2H-pyridazin-3-one suspension is cooled to a temperature of at least 40° C. The resulting suspension can be subjected to more cycles of heating and cooling for shorter periods. Preferably, the resulting solution is heated to about 60° C. for at least an hour and then cooled to about 40°

C. for at least an hour. Once the heating and cooling cycles are complete, the 2-(6-{2-[(2R)-2-methyl-1-pyrrolidin-1-yl]-ethyl}-2-naphthalen-2-yl)-2H-pyridazin-3-one suspension is cooled to a lower temperature to afford a suspension that can be filtered to provide 2-(6-{2-[(2R)-2-methyl-1-pyrrolidin-1-yl]-ethyl}-2-naphthalen-2-yl)-2H-pyridazin-3-one citrate salt crystals. Preferably, the suspension is cooled to less than ambient temperature. The solution is typically from about 10° C. to about 0° C. Typically, a solution of at least 5° C. is suitable for filtering.

The suspension is filtered by any suitable method to obtain a clear filtrate. The preferred method for filtering is vacuum filtration under cooled conditions with a temperature of about 10° C. to about 0° C. Typically, a solution of at least 5° C. is suitable for filtering.

The suspension is filtered by any method to obtain a clear filtrate. The preferred method for filtering is vacuum filtration under cooled conditions with a temperature of about 10° C. to about 0° C. The cooled suspension is slowly poured into a suitable container lined with a medium for separating the filtrate from the solid. The solid, or wet cake, can be dried under at least ambient conditions with or without vacuum filtration to provide the desired 2-(6-{2-[(2R)-2-methyl-1-pyrrolidin-1-yl]-ethyl}-2-naphthalen-2-yl)-2H-pyridazin-3-one citrate.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

Methods of the Invention

Compounds and compositions of the invention are useful for modulating the effects of histamine-3 receptors. In particular, the compounds and compositions of the invention can be used for treating and preventing disorders modulated by the histamine-3 receptors. Typically, such disorders can be ameliorated by selectively modulating the histamine-3 receptors in a mammal, preferably by administering a compound or composition of the invention, either alone or in combination with another active agent as part of a therapeutic regimen.

The compounds of the invention, including but not limited to those specified in the examples, possess an affinity for the histamine-3 receptors. As histamine-3 receptor ligands, the compounds of the invention may be useful for the treatment and prevention of diseases or conditions such as acute myocardial infarction, Alzheimer's disease, asthma, attention-deficit hyperactivity disorder, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, metabolic syndrome, mild cognitive impairment, migraine, mood and attention alteration, motion sickness, narcolepsy, neurogenic inflammation, obesity, obsessive compulsive disorder, pain, Parkinson's disease, polycystic ovary syndrome, schizophrenia, cognitive deficits of schizophrenia, seizures, septic shock, Syndrome X, Tourette's syndrome, vertigo, and sleep disorders.

The ability of the compounds of the invention, including, but not limited to, those specified in the examples, to treat septic shock and cardiovascular disorders, in particular, acute myocardial infarction may be demonstrated by Imamura et al., Circ. Res., 78:475–481 (1996); Imamura et. al., Circ. Res., 78:863–869 (1996); R. Levi and N. C. E. Smith, "Histamine $H_3$-receptors: A new frontier in myocardial ischemia", J. Pharm. Exp. Ther., 292:825–830 (2000); and Hatta, E., K. Yasuda and R. Levi, "Activation of histamine $H_3$ receptors inhibits carrier-mediated norepinephrine release in a human model of protracted myocradial ischemia", J. Pharm. Exp. Ther., 283:494–500 (1997).

The ability of the compounds of the invention, including, but not limited to, those specified in the examples, to treat sleep disorders, in particular, narcolepsy may be demonstrated by Lin et al., Brain Res., 523:325–330 (1990); Monti, et al., Neuropsychopharmacology 15:31–35 (1996); Sakai, et al., Life Sci., 48:2397–2404 (1991); Mazurkiewicz-Kwilecki and Nsonwah, Can. J. Physiol. Pharmacol., 67:75–78 (1989); P. Panula, et al., Neuroscience 44:465–481 (1998); Wada, et al., Trends in Neuroscience 14:415 (1991); and Monti, et al., Eur. J. Pharmacol. 205:283 (1991).

The ability of the compounds of the invention, including, but not limited to, those specified in the examples, to treat cognition and memory process disorders may be demonstrated by Mazurkiewicz-Kwilecki and Nsonwah, Can. J. Physiol. Pharmacol., 67:75–78 (1989); P. Panula, et al., Neuroscience, 82:993–997 (1997); Haas, et al., Behav. Brain Res., 66:41–44 (1995); De Almeida and Izquierdo, Arch. Int. Pharmacodyn., 283:193–198 (1986); Kamei et al., Psychopharmacology, 102:312–318 (1990); Kamei and Sakata, Jpn. J. Pharmacol., 57:437–482 (1991); Schwartz et al., Psychopharmacology, The fourth Generation of Progress. Bloom and Kupfer (eds). Raven Press, New York, (1995) 397; and Wada, et al., Trends in Neurosci., 14:415 (1991).

The ability of the compounds of the invention, including, but not limited to, those specified in the examples, to treat attention-deficit hyperactivity disorder (ADHD) may be demonstrated by Shaywitz et al., Psychopharmacology, 82:73–77 (1984); Dumery and Blozovski, Exp. Brain Res., 67:61–69 (1987); Tedford et al., J. Pharmacol. Exp. Ther., 275:598–604 (1995); Tedford et al., Soc. Neurosci. Abstr., 22:22 (1996); and Fox, et al., Behav. Brain Res., 131: 151–161 (2002).

The ability of the compounds of the invention, including, but not limited to, those specified in the examples, to treat seizures, in particular, epilepsy may be demonstrated by Yokoyama, et al., Eur. J. Pharmacol., 234:129 (1993); Yokoyama and Iinuma, CNS Drugs 5:321 (1996); Onodera et al., Prog. Neurobiol., 42:685 (1994); R. Leurs, R. C. Vollinga and H. Timmerman, "The medicinal chemistry and therapeutic potential of ligands of the histamine $H_3$ receptor", Progress in Drug Research 45:170–165, (1995); Leurs and Timmerman, Prog. Drug Res., 39:127 (1992); The Histamine $H_3$ Receptor, Leurs and Timmerman (eds), Elsevier Science, Amsterdam, The Netherlands (1998); and H. Yokoyama and K. Iinuma, "Histamine and Seizures: Implications for the treatment of epilepsy", CNS Drugs, 5(5):321–330 (1995).

The ability of the compounds of the invention, including, but not limited to, those specified in the examples, to treat motion sickness, Alzheimer's disease, and Parkinson's disease may be demonstrated by Onodera, et al., Prog. Neurobiol., 42:685 (1994); Leurs and Timmerman, Prog. Drug Res., 39:127 (1992); and The Histamine $H_3$ Receptor, Leurs and Timmerman (eds), Elsevier Science, Amsterdam, The Netherlands (1998).

The ability of the compounds of the invention, including, but not limited to, those specified in the examples, to treat narcolepsy, schizophrenia, depression, and dementia may be demonstrated by R. Leurs, R. C. Vollinga and H. Timmerman, "The medicinal chemistry and therapeutic potential of ligands of the histamine $H_3$ receptor", Progress in Drug Research 45:170–165 (1995); The Histamine $H_3$ Receptor, Leurs and Timmerman (eds), Elsevier Science, Amsterdam, The Netherlands (1998); and Perez-Garcia C, et. al., and Psychopharmacology (Berl) 142(2):215–20 (February, 1999).

The ability of the compounds of the invention, including, but not limited to, those specified in the examples, to treat sleep disorders, cognitive dysfunction, mood and attention alteration, vertigo and motion sickness, and treatment of cognitive deficits in psychiatric disorders may be demonstrated by Schwartz, Physiol. Review 71:1–51 (1991).

The ability of the compounds of the invention, including, but not limited to, those specified in the examples, to treat mild cognitive impairment, deficits of memory, deficits of learning and dementia may be demonstrated by C. E. Tedford, in "The Histamine $H_3$ Receptor: a target for new drugs", the Pharmacochemistry Library, vol. 30 (1998) edited by R. Leurs and H. Timmerman, Elsevier (New York). p. 269 and references also contained therein.

The ability of the compounds of the invention, including, but not limited to, those specified in the examples, to treat obesity may be demonstrated by Leurs, et al., Trends in Pharm. Sci., 19:177–183 (1998); E. Itoh, M. Fujimiay, and A. Inui, "Thioperamide, A histamine $H_3$ receptor antagonist, powerfully suppresses peptide YY-induced food intake in rats," Biol. Psych., 45(4):475–481 (1999); S. I. Yates, et al., "Effects of a novel histamine $H_3$ receptor antagonist, GT-2394, on food intake and weight gain in Sprague-Dawley rats," Abstracts, Society for Neuroscience, 102.10: 219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000).

The ability of the compounds of the invention, including, but not limited to, those specified in the examples, to treat inflammation and pain may be demonstrated by Phillips, et al., Annual Reports in Medicinal Chemistry 33:31–40 (1998).

The ability of the compounds of the invention, including, but not limited to, those specified in the examples, to treat migraine may be demonstrated by R. Leurs, R. C. Vollinga and H. Timmerman, "The medicinal chemistry and therapeutic potential of ligands of the histamine $H_3$ receptor," Progress in Drug Research 45:170–165 (1995); Matsubara, et al., Eur. J. Pharmacol., 224:145 (1992); and Rouleau, et al., J. Pharmacol. Exp. Ther., 281:1085 (1997).

The ability of the compounds of the invention, including, but not limited to, those specified in the examples, to treat cancer, in particular, melanoma, cutaneous carcinoma and medullary thyroid carcinoma may be demonstrated by Adam Szelag, "Role of histamine $H_3$-receptors in the proliferation of neoplastic cells in vitro," Med. Sci. Monit., 4(5):747–755

(1998); and C. H. Fitzsimons, et al., "Histamine receptors signalling in epidermal tumor cell lines with H-ras gene alterations," Inflammation Res., 47 (Suppl 1):S50–S51 (1998).

The ability of the compounds of the invention, including, but not limited to, those specified in the examples, to treat vestibular dysfunctions, in particular, Meniere's disease may be demonstrated by R. Leurs, R. C. Vollinga and H. Timmerman, "The medicinal chemistry and therapeutic potential of ligands of the histamine $H_3$ receptor," Progress in Drug Research 45:170–165 (1995), and Pan, et al., Methods and Findings in Experimental and Chemical Pharmacology 21:771–777 (1998).

The ability of the compounds of the invention, including, but not limited to, those specified in the examples, to treat asthma may be demonstrated by A. Delaunois A., et al., "Modulation of acetylcholine, capsaicin and substance P effects by histamine $H_3$ receptors in isolated perfused rabbit lungs," European Journal of Pharmacology 277(2–3):243–250 (1995); and Dimitriadou, et al., "Functional relationship between mast cells and C-sensitive nerve fibres evidenced by histamine $H_3$-receptor modulation in rat lung and spleen," Clinical Science 87(2):151–163 (1994).

The ability of the compounds of the invention, including, but not limited to, those specified in the examples, to treat allergic rhinitis may be demonstrated by McLeod, et al., Progress in Resp. Research 31:133 (2001).

Compounds of the invention are particularly useful for treating and preventing a condition or disorder affecting the memory or cognition, for example Alzheimer's disease, attention-deficit hyperactivity disorder, schizophrenia, or the cognitive deficits of schizophrenia.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

The compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 30 mg/kg/day. For purposes of oral administration, more preferable doses can be in the range of from about 0.01 to about 0.1 mg/kg/day. If desired, the effective daily dose can be divided into multiple doses for purposes of administration; consequently, single dose compositions may contain such amounts or submultiples thereof to make up the daily dose.

The invention will be better understood in connection with the following Examples, which are intended as an illustration of and not a limitation upon the scope of the invention. Variations and changes which are obvious to one skilled in the art are intended to be within the scope and nature of the invention.

EXAMPLES

Example 1

Preparation of 2-(6-{2-[(2R)-2-Methyl-1-pyrrolidin-1-yl]-ethyl}-2-naphthalen-2-yl)-2H-pyridazin-3-one Step 1: Preparation of Trifluoro-methanesulfonic acid 6-bromo-naphthalen-2-yl ester (2)

To a mixture of 6-bromo-naphthalen-2-ol (24 g, 107.6 mmol) in toluene (600 mL) was added a solution of potassium phosphate (181 g) in $H_2O$ (423 mL). The mixture was cooled to –5° C.~0° C., to the mixture was added trifluromethanesulfonic anhydride (22.6 mL, 134.5 mmol) dropwise keeping the temperature below 0° C. The resulting mixture was stirred at 0° C. for 3 h. The aqueous layer was separated and the organic layer was washed with 5% $NaHCO_3$ (400 mL), brine (400 mL) and dried over $Na_2SO_4$. The organic layer was then concentrated under reduced pressure to give an oil which was further dried under high vacuum to afford 35.6 g product as an oil which solidified upon standing in a refrigerator. $^1H$ NMR (400 MHz, $CDCl_3$) d 7.91 (s,1H), 7.69 (d, 1H), 7.50–7.61 (m, 2H), 7.50–7.52 (dd,1H), 7.24–7.27 (dd, 1H). $^{13}C$ NMR (400 MHz, $CDCl_3$) d 146.78, 132.97, 131.44, 130.77, 129.69, 129.39, 129.24, 121.11, 120.45, 120.10, 119.09, 116.93. $[M^+NH_4^-H_2O]^+$ at m/z 356.

Step 2: Preparation of 2-Bromo-6-vinyl-naphthalene (3)

A mixture of trifluoro-methanesulfonic acid 6-bromo-naphthalen-2-yl ester (2) (3.0 g, 8.45 mmol), potassium vinyltrifluoroborate (1.4 g, 11.83 mmol) in EtOH (84 mL) and a 1.0 M aqueous solution of cesium carbonate (17 mL) was purged with nitrogen, to the mixture was added tetrakis (triphenylphosphine)palladium (244 mg, 0.2 mmol) followed by triethylamine (2.3 mL, 17 mmol). The mixture was heated to 45° C. for 16 h under nitrogen and cooled to room temperature. To the mixture was added $H_2O$ (84 mL), the resulting suspension was stirred at room temperature for 30 min. and filtered. The wet cake was washed with $H_2O$ (30 mL) and dried in the vacuum oven at 45° C. for 16 h to give 1.9 g product. The product is used in the next step without further purification. $^1H$ NMR (400 MHz, $CDCl_3$) d 7.86 (d, 1H), 7.54–7.61 (m, 4H), 7.42–7.44 (dd, 1H), 6.73–6.80 (dd, 1H). $^{13}C$ NMR (400 MHz, $CDCl_3$) d 136.18, 135.12, 133.77, 131.62, 129.42, 129.32, 129.29, 126.93, 125.84, 124.00, 119.55, 114.54. $[M+H]^+$ at m/z 233.

Step 3: Preparation of 1-[2-(6-Bromo-naphthalen-2-yl)-ethyl]-2-methyl-pyrrolidine (4)

To a cooled solution of 2-methylpyrrolidine (2.0 mL, 20 mmol) in THF (30 mL) at –15° C. was added n-BuLi (1.6 M in hexane, 4.0 mL, 6.4 mmol) dropwise keeping the temperature below –10° C. The resulting mixture was stirred at −15° C. for 10 min. To the cooled solution was added a solution of 2-bromo-6-vinyl-naphthalene (3) (2.33 g, 10.0 mmol) in THF (30 mL) dropwise keeping the temperature below −15° C. The resulting mixture was stirred at −15° C. for 5 min. and quenched with $H_2O$ (1 mL) and then poured into 5% $Na_2CO_3$ (80 mL). To the mixture was added EtOAc (80 mL), and organic was separated, the aqueous layer was extracted with EtOAc (30 mL). The combined organic layer was washed with brine and treated with activated carbon, dried over $Na_2SO_4$ and concentrated. The residue was then further dried under high vacuum to give 2.47 g product. The crude product was used in the next step without further purification. $^1H$ NMR (400 MHz, $CDCl_3$) d 7.86 (d, 1H), 7.53–7.59 (m, 3H), 7.40–7.42 (dd,1H), 7.28–7.30 (dd, 1H), 3.04–3.22 (m, 1H), 3.98–3.04 (m, 1H), 2.85–2.91 (m, 2H), 2.23–2.33 (m, 2H), 2.14 (q, 1H), 1.81–1.88 (m, 1H), 1.62–1.78 (m, 2H), 1.32–1.39 (m, 1H), 1.04 (d, 3H). $^{13}C$ NMR (400 MHz, $CDCl_3$) d 138.50, 132.75, 131.65, 129.29, 128.90, 128.76, 128.21, 126.63, 126.34, 118.72, 60.11, 55.88, 54.15, 35.78, 32.93, 21.98, 19.28. $[M+H]^+$ at m/z 319.

Step 4: Preparation of 2-{6-[2-(2-methyl-pyrrolidin-1-yl)-ethyl]-naphthalen-2-yl}-2H-pyridazin-3-one To a 60 mL pressure tube were added 1-[2-(6-bromo-naphthalen-2-yl)-ethyl]-2-methyl-pyrrolidine (1.94 g, 6.1 mmol), (2H)-pyridazin-3-one (878 mg, 9.2 mmol), copper (I) chloride (30.1 mg, 0.30 mmol), 8-hydroxyquinoline (44.2 mg, 0.30 mmol), powdered potassium carbonate (1.27 g, 9.2 mmol), and DMF (10 mL). The reaction mixture was evacuated, and purged with nitrogen. The tube was sealed, heated to ~140° C., and mixed overnight. The mixture was cooled to 25° C., diluted with ethyl acetate (40 mL), concentrated ammonium hydroxide (4 mL) and 25% brine (40 mL). The mixture was mixed for 15 minutes, and filtered through a pad of diatomaceous earth. The upper organic was washed with 25% brine (40 mL×3), dried over $Na_2SO_4$, and filtered. The filtrate was concentrated to dryness to obtain the crude product, which is 2-{6-[2-(2-methyl-pyrrolidin-1-yl)-ethyl]-naphthalen-2-yl}-2H-pyridazin-3-one free base. $[M+H]^+$ at m/z 334.

The crude product can be purified by crystallizing its HBr salt, then converting the HBr salt to the desired citrate salt.

Example 2

Preparation of 2-(6-{2-[(2R)-2-Methyl-1-pyrrolidin-1-yl]-ethyl}-2-naphthalen-2-yl)-2H-pyridazin-3-one Citrate Salt (2:1 ratio)

Citric acid (10 kg) was dissolved in ethanol (44.8 kg). The citric acid solution was added to a solution of the 2-(6-{2-[(2R)-2-methyl-1-pyrrolidin-1-yl]-ethyl}-2-naphthalen-2-yl)-2H-pyridazin-3-one free base (5.80 kg) in ethanol (148.8 kg). The reaction mixture was heated to 40° C. A slurry of seed crystals (0.1 kg) in ethanol (1.4 kg) was then added. The suspension was stirred at 40° C. for no less than 4 h as the citrate salt crystallized. The suspension was subjected to heat/cool cycles (2 times) to grow larger crystals. One heat/cool cycle was as follows: heat to 60° C. and mix for no less than 1 h, slowly cool to 40° C. and mix for no less than 1 h. The suspension was then cooled to no less than 5° C. and filtered. The wet cake was washed with ethanol (55 kg) and dried under vacuum to yield 10.7 kg as a white solid. Melting point=143–149° C. (analyzed by DSC); ee=99.0% by chiral HPLC; $^1H$ NMR (DMSO-$d_6$) δ 8.2–8.1 (2H, m), 8.0–7.9 (2H, t), 7.9–7.8 (1H, s), 7.7–7.6 (1H, dd), 7.6–7.5 (2H, m), 7.2–7.1 (1H, dd), 3.7–3.5 (2H, m), 3.5–3.4 (1H, m), 3.4–3.1 (4H), 2.7–2.5 (8H, dd), 2.1–1.9 (2H, m), 1.7–1.6 (1H, m), 1.4–1.3 (3H, d); $^{13}C$ NMR (DMSO-$d_6$) δ 175.1, 170.6, 158.9, 138.4, 137.2, 135.3, 132.0, 128.0, 127.5, 127.3, 126.4, 123.7, 123.4, 71.7, 63.1, 52.6, 43.6, 31.4, 31.0, 21.2, 15.8 with 3 peaks overlapping. MS-ESI $(M+H)^+$ at m/z 334.2 (fragment at 210.0).

Example 3

Preparation of 2-(6-{2-[(2R)-2-Methyl-1-pyrrolidin-1-yl]-ethyl}-2-naphthalen-2-yl)-2H-pyridazin-3-one Citrate Salt (1:1 ratio)

Citric acid (1.16 g, 1.1 mol) in acetonitrile (15 mL) to a solution of 2-(6-{2-[(2R)-2-methyl-1-pyrrolidin-1-yl]-ethyl}-2-naphthalen-2-yl)-2H-pyridazin-3-one free base (1.67 g, 5 mmol) in acetonitrile/methanol (17 mL, 12 mL/g total volume) to form a cloudy solution. The cloudy solution was heated to 80° C. to dissolve any solids. The solution was slowly cooled at room temperature (~22° C.) and the biphasic oil-solution crystallized. The salt suspension was cooled to ~0° C. and filtered. The wet cake was dried in a vacuum oven (40–50° C.), isolating 1.16 g of the citrate salt. Melting point=103–113° C. (analyzed by DSC); PXRD 2-theta angles: 7.658°±0.1°, 9.560°±0.1°, 11.520°±0.1°, 19.437°±0.1° and 21.440°±0.1°; $^1H$ NMR (DMSO-d6) d 8.1 (2H, m), 8.0–7.9 (2H, dd), 7.9 (1H, s), 7.7–7.6 (1H, dd), 7.6–7.5 (2H, m), 7.2–7.1 (1H, dd), 3.6–3.5 (2H, m), 3.4–3.3 (1H, m), 3.2–3.0 (4H), 2.6–2.5 (from citric acid, 4H, dd), 2.2–2.1 (1H, m), 2.0–1.8 (2H, m), 1.7–1.5 (1H, m), 1.4–1.3 (3H, d).

Alternatively, the citrate salt (1:1 ratio) also was crystallized from ethanol (12 mL/g).

Example 4

Preparation of 2-(6-{2-[(2R)-2-Methyl-1-pyrrolidin-1-yl]-ethyl}-2-naphthalen-2-yl)-2H-pyridazin-3-one HBr (Form I polymorph)

A solution of 48% HBr in water (1.29 g, 1.05 mol) was added to a solution of 2-(6-{2-[(2R)-2-methyl-1-pyrrolidin-1-yl]-ethyl}-2-naphthalen-2-yl)-2H-pyridazin-3-one free base (2.4 g, 7 mmol) in isopropanol (50 mL, 17 mL/g). The salt crystallized from the solution while stirring at room temperature (~22° C.). The suspension was filtered, washed with isopropanol, and dried in a vacuum oven (~45° C.). Isolated 2.98 g solid. Melting point=204–210° C. (analyzed by DSC); PXRD 2-theta angles: 12.498°±0.1°, 15.554°±0.1°, 16.550°±0.1°, 18.180°±0.1° and 20.771°±0.1°.

Example 5

Preparation of 2-(6-{2-[(2R)-2-Methyl-1-pyrrolidin-1-yl]-ethyl}-2-naphthalen-2-yl)-2H-pyridazin-3-one HBr (Form II polymorph)

A 48% solution of HBr in water (1.65 kg, 1.1 mol) was added to a solution of the 2-(6-{2-[(2R)-2-methyl-1-pyrrolidin-1-yl]-ethyl}-2-naphthalen-2-yl)-2H-pyridazin-3-one free base (2.7 kg, 8.1 mol) in 3A ethanol (~75 L, 8 L/kg). The solution was heated to 60° C. to dissolve any precipitated HBr salt. The resulting solution was cooled to 50° C. HBr salt (Form II) seed crystals (60 g, 2 weight % based on the theoretical yield of salt formation) were slurried in ethanol (0.3 kg, approximately 6 mL/g) and added to the free base solution. The resulting suspension was slowly cooled to −5° C. The suspension was filtered, washed with isopropyl acetate (12 kg, 4 mL/g), and dried under vacuum (~50° C.). Isolated 3.0 kg solid. Melting point=206–209° C. (by DSC); PXRD 2-theta angles: 13.884°±0.1°, 17.138°±0.1°, 18.860°±0.1°, 20.591°±0.1° and 25.584°±0.1°.

Example 6

Preparation of 2-(6-{2-[(2R)-2-Methyl-1-pyrrolidin-1-yl]-ethyl}-2-naphthalen-2-yl)-2H-pyridazin-3-one Maleate Salt A solution of maleic acid (0.55 g, 1.05 mol) in ethanol was added to a solution of the 2-(6-{2-[(2R)-2-methyl-1-pyrrolidin-1-yl]-ethyl}-2-naphthalen-2-yl)-2H-pyridazin-3-one free base (1.5 g, 4.5 mmol) in ethanol (20 mL total volume, approximately 10 mL/g). Heptanes were then added (15 mL, ~10 mL/g) to the mixture under ambient conditions overnight. The suspension was cooled to approximately 0° C. Filtered the suspension, washed with heptanes (2 mL) and dried under vacuum (~45° C.). Isolated 1.8 g solid. Melting point=110–114° C. (by DSC); PXRD 2-theta angles: 5.353°±0.1°, 11.017°±0.1°, 16.768°±0.1°, 15.576°±0.1° and 21.554°±0.1°.

Example 7

Preparation of 2-(6-{2-[(2R)-2-Methyl-1-pyrrolidin-1-yl]-ethyl}-2-naphthalen-2-yl)-2H-pyridazin-3-one Fumarate Salt A solution of fumaric acid (0.18 g, 1.05 mol) in ethanol was added to a solution of the 2-(6-{2-[(2R)-2-methyl-1-pyrrolidin-1-yl]-ethyl}-2-naphthalen-2-yl)-2H-pyridazin-3-one free base (0.5 g, 1.5 mmol) in ethanol (8 mL, ~10 mL/g total volume). The solution was stirred under ambient conditions overnight. The suspension was cooled to approximately 0° C. The suspension was filtered, washed with ethanol (1 mL), and dried under vacuum (~45° C.). Isolated ~0.5 g product. Melting point=125–130° C. (by DSC); PXRD 2-theta angles: 4.614°±0.1°, 13.881°±0.1°, 18.086°±0.1°, 18.580°±0.1° and 23.748°±0.1°.

Example 8

Preparation of 2-(6-{2-[(2R)-2-Methyl-1-pyrrolidin-1-yl]-ethyl}-2-naphthalen-2-yl)-2H-pyridazin-3-one Salicylate Salt Salicylic acid (0.05 g, 1.1 mol) in methanol (0.25 mL) with was mixed with 2-(6-{2-[(2R)-2-methyl-1-pyrrolidin-1-yl]-ethyl}-2-naphthalen-2-yl)-2H-pyridazin-3-one free base (0.1 g, 0.3 mmol) in ethyl acetate (2 mL) at 50° C. The solution was cooled to ambient temperature. The suspension was filtered and dried under vacuum (~45° C.). Isolated 0.09 g product. Melting point=163–165° C. (by DSC); PXRD 2-theta angles: 4.241°±0.1°, 8.516°±0.1°, 12.854°±0.1°, 14.030°±0.1° and 15.208°±0.1°.

Example 9

Preparation of 2-(6-{2-[(2 R)-2-Methyl-1-pyrrolidin-1-yl]-ethyl}-2-naphthalen-2-yl)-2H-pyridazin-3-one Sulfate Salt Concentrated sulfuric acid (~0.2 mL, ~1.1 mol) was mixed with 2-(6-{2-[(2R)-2-methyl-1-pyrrolidin-1-yl]-ethyl}-2-naphthalen-2-yl)-2H-pyridazin-3-one free base (0.1 g, 0.3 mmol) in isopropanol (2 mL) under ambient conditions. A suspension formed form a biphasic oil-solution. The suspension was filtered and dried under vacuum (~45° C.). Isolated 0.03 g product. Melting point=265–268° C. (by DSC); PXRD 2-theta angles: 12.447°±0.1°, 13.298°±0.1°, 14.521°±0.1°, 16.399°±0.1° and 17.718°±0.1°.

Example 10

Preparation of 2-(6-{2-[(2R)-2-Methyl-1-pyrrolidin-1-yl]-ethyl}-2-naphthalen-2-yl)-2H-pyridazin-3-one Tosylate Salt p-Toluenesulfonic acid (0.06 g, 1.1 molar equivalents) was mixed with 2-(6-{2-[(2R)-2-methyl-1-pyrrolidin-1-yl]-ethyl}-2-naphthalen-2-yl)-2H-pyridazin-3-one free base (0.1 g, 0.3 mmol) in acetone (2 mL) at 50° C. The solution was concentrated to minimum volume (<0.5 mL) and cooled to 0° C. A suspension formed from the biphasic oil-solution. Heptane was added to the suspension, and filtered. Isolated 0.05 g product. Melting point=58–70° C. (by DSC); PXRD 2-theta angles: 10.599°±0.1°, 12.179°±0.1°, 14.019°±0.1°, 17.240°±0.1° and 19.379°±0.1°.

What is claimed is:

1. A method of preparing crystalline 2-(6-{2-[(2R)-2-methyl-1-pyrrolidin-1-yl]-ethyl}-2-naphthalen-2-yl)-2H-pyridazin-3-one citrate, comprising the steps of:
    (a) dissolving 2-(6-{2-[(2R)-2-methyl-1-pyrrolidin-1-yl]-ethyl}-2-naphthalen-2-yl)-2H-pyridazin-3-one in a solution of citric acid and ethanol;
    (b) heating the reaction mixture to a temperature of about 40° C. to about 65° C.;
    (c) adding a seed slurry of 2-(6-{2-[(2R)-2-methyl-1-pyrrolidin-1-yl]-ethyl}-2-naphthalen-2-yl)-2H-pyridazin-3-one crystals;
    (d) cooling the resulting solution to less than 5° C. for at least one hour to provide a suspension; and
    (e) filtering the resulting suspension.

2. A method of preparing a 2-{6-[2-(2-methyl-pyrrolidin-1-yl)-ethyl]-naphthalen-2-yl}-2H-pyridazin-3-one, comprising the steps of:
    (a) converting the trifluoro-methanesulfonic acid 6-bromo-naphthalen-2-yl ester to 2-bromo-6-vinyl-naphthalene;
    (b) reacting 2-bromo-6-vinyl-naphthalene with 2-methylpyrrolidine in the presence of n-butyllithium to provide 1-[2-(6-bromo-naphthalen-2-yl)-ethyl]-2-methyl-pyrrolidine; and
    (c) reacting 1-[2-(6-bromo-naphthalen-2-yl)-ethyl]-2-methyl-pyrrolidine with 2H-pyridazin-3-one.

3. The method of claim 2, wherein the trifluoro-methanesulfonic acid 6-bromo-naphthalen-2-yl ester is obtained by:
    (a) providing 6-bromo-naphthalen-2-ol; and
    (b) reacting 6-bromo-naphthalen-2-ol with a suitable trifluoromethanesulfonic reagent.

4. The method of claim 1, wherein the 2-(6-{2-[(2R)-2-methyl-1-pyrrolidin-1-yl]-ethyl}-2-naphthalen-2-yl)-2H-pyridazin-3-one is obtained by:
    (a) converting the trifluoro-methanesulfonic acid 6-bromo-naphthalen-2-yl ester to 2-bromo-6-vinyl-naphthalene;
    (b) reacting 2-bromo-6-vinyl-naphthalene with (2R)-methylpyrrolidine in the presence of n-butyllithium to provide 1-[2-(6-bromo-naphthalen-2-yl)-ethyl]-2-methyl-pyrrolidine; and
    (c) reacting 1-[2-(6-bromo-naphthalen-2-yl)-ethyl]-(2R)-methyl-pyrrolidine with 2H-pyridazin-3-one.

* * * * *